(12) United States Patent
Link et al.

(10) Patent No.: US 11,998,606 B2
(45) Date of Patent: Jun. 4, 2024

(54) COMPOUNDS AND METHODS FOR SELECTIVE PROTEOLYSIS OF GLUCOCORTICOID RECEPTORS

(71) Applicant: Board of Regents, The University of Texas System, Austin, TX (US)

(72) Inventors: James T. Link, Pearland, TX (US); Yonathan Lissanu Deribe, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 868 days.

(21) Appl. No.: 17/047,267

(22) PCT Filed: Apr. 12, 2019

(86) PCT No.: PCT/US2019/027163
§ 371 (c)(1),
(2) Date: Oct. 13, 2020

(87) PCT Pub. No.: WO2019/200217
PCT Pub. Date: Oct. 19, 2019

(65) Prior Publication Data
US 2021/0361773 A1      Nov. 25, 2021

Related U.S. Application Data

(60) Provisional application No. 62/657,598, filed on Apr. 13, 2018.

(51) Int. Cl.
A61K 47/55     (2017.01)
A61K 45/06     (2006.01)
A61K 47/54     (2017.01)

(52) U.S. Cl.
CPC ............ *A61K 47/545* (2017.08); *A61K 45/06* (2013.01); *A61K 47/55* (2017.08)

(58) Field of Classification Search
CPC ....... A61K 47/545; A61K 47/55; A61K 45/06
See application file for complete search history.

(56) References Cited

U.S. PATENT DOCUMENTS

2007/0027117 A1   2/2007   Bishop
2016/0235731 A1   8/2016   Bradner
2016/0289261 A1 * 10/2016  Arora .................... A61K 45/06

FOREIGN PATENT DOCUMENTS

| WO | 2013106643 | 7/2013 |
| WO | 2017112902 | 6/2017 |
| WO | 2017112904 | 6/2017 |
| WO | 2013/106643 | * 10/2019 |
| WO | 2019200217 | 10/2019 |

OTHER PUBLICATIONS

Petta, Microbiology and Molecular Biology Reviews, vol. 80(2), 2016, 495-522. (Year: 2016).*
Smoak, Mechanisms of Ageing and Development, 125, (2004), 697-706. (Year: 2004).*
Baschant, J of Steroid Biochemistry & Molecular Biology, 120, (2010), 69-75. (Year: 2010).*
International Application No. PCT/US2019/027163; International Preliminary Report on Patentability, dated Oct. 22, 2020; 5 pages.
International Application No. PCT/US2019/027163; International Search Report and Written Opinion of the International Searching Authority, dated Jun. 28, 2019; 7 pages.
Von Gelden, T. et al., "Liver-Selective Glucocorticoid Antagonists: A Novel Treatment for Type 2 Diabetes", J Med Chem., 47(17):4213-30, (2004).
Zengerle, M. et al., "Selective Small Molecule Induced Degradation of the BET Bromodomain Protein BRD4", ACS Chem Biol., 10(8):1770-7, (2015).

* cited by examiner

*Primary Examiner* — D Margaret M Seaman
(74) *Attorney, Agent, or Firm* — Cynthia Hathaway; Lauren L. Stevens; Erik M. Larsen

(57) ABSTRACT

The present disclosure relates to steroidal glucocorticoid receptor (GR) ligands and related compositions that degrade the GR and/or modulate its activity that may be utilized as pharmaceuticals for the treatment of diseases including cancer.

28 Claims, 8 Drawing Sheets

FIG. 1
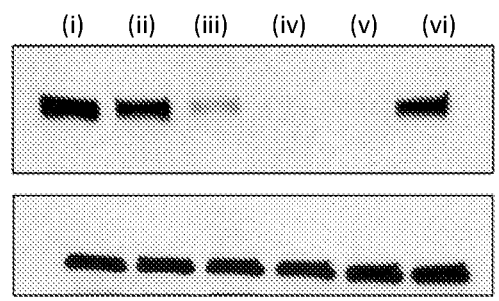
FIG. 1(a)
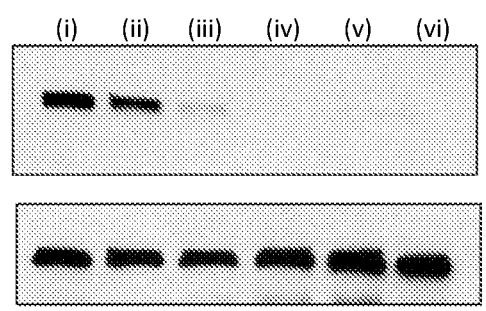
FIG. 1(b)
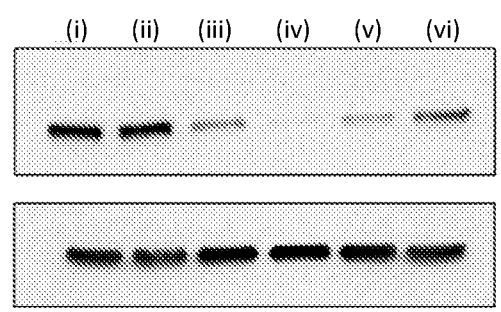
FIG. 1(c)

FIG. 2
(i) (ii) (iii)
(iv) (v)
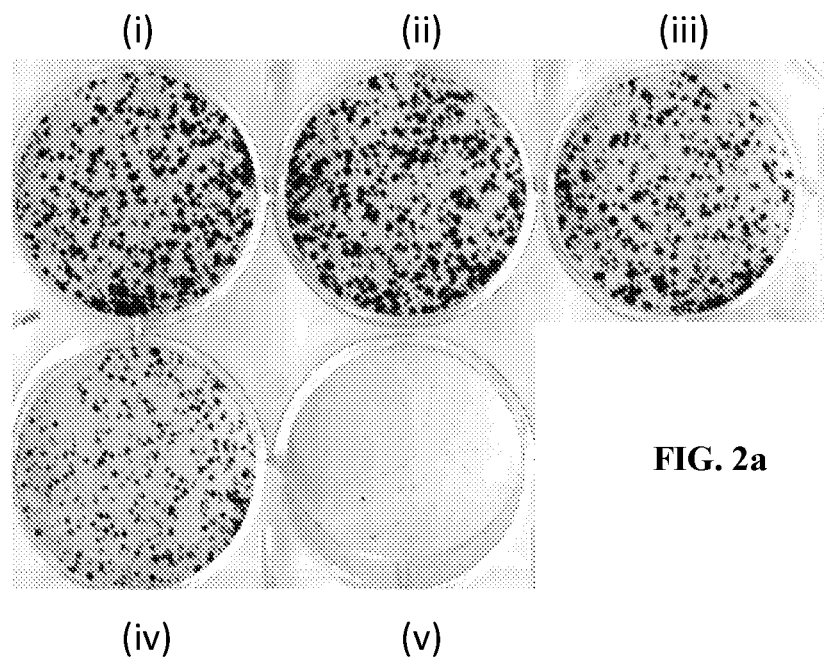
FIG. 2a
(i) (ii) (iii)
(iv) (v)
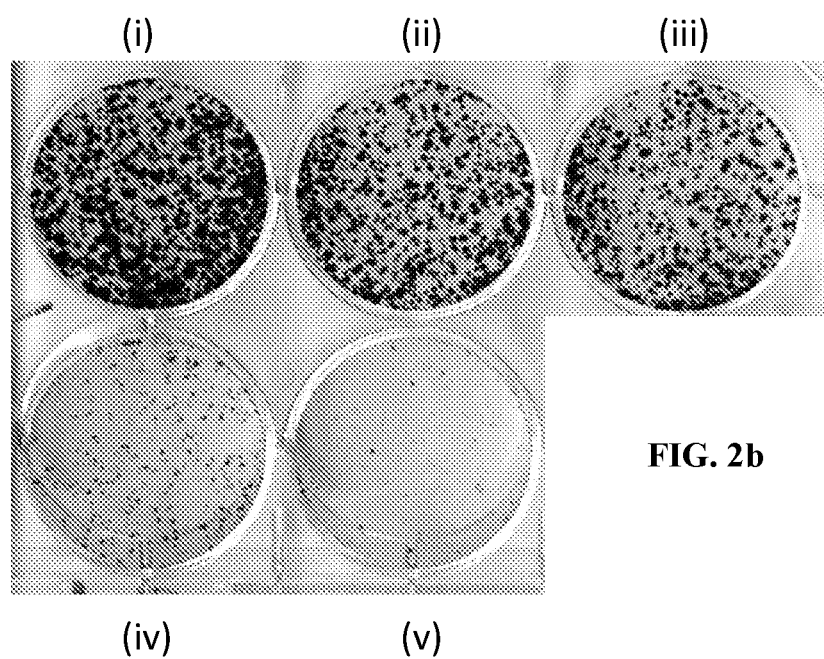
FIG. 2b FIG. 4
FIG. 4a
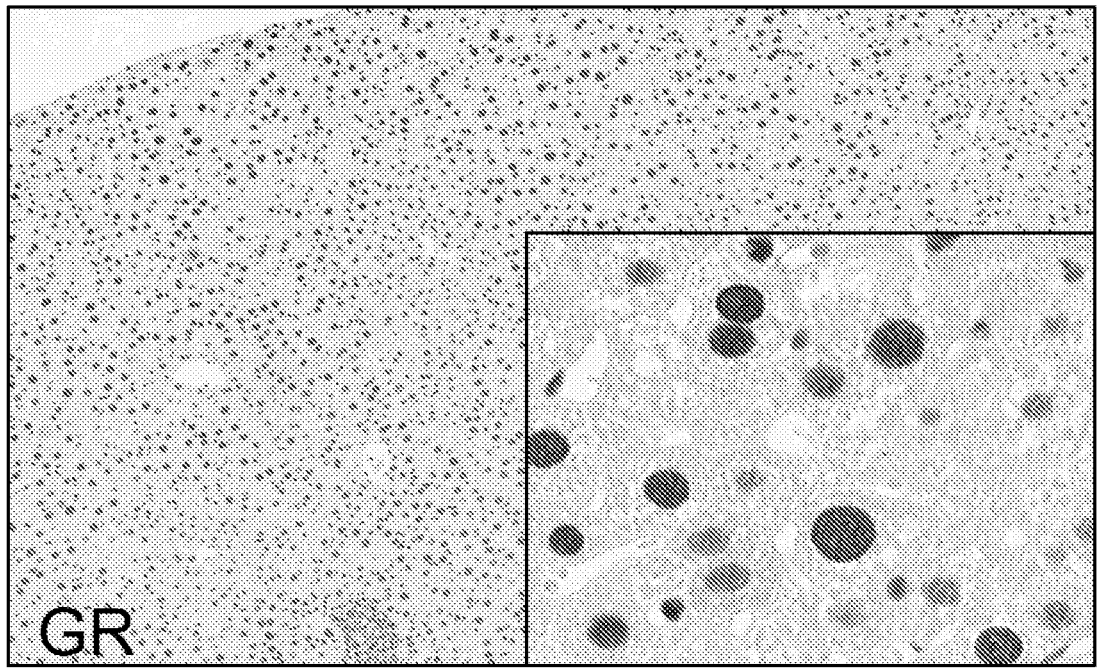
FIG. 4b
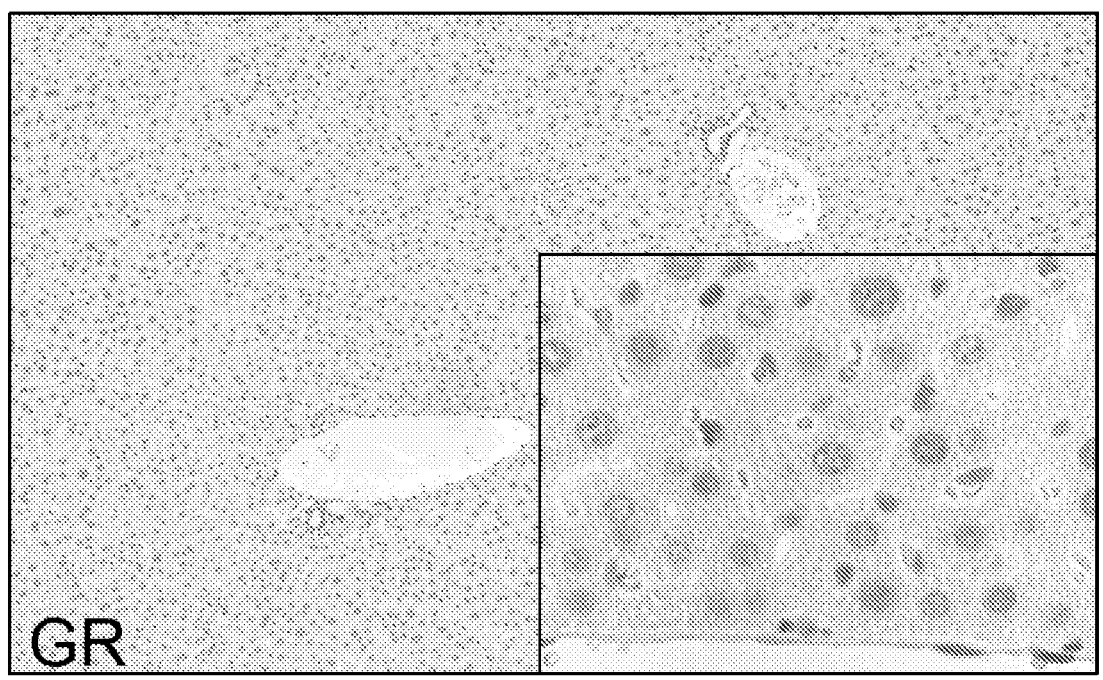

COMPOUNDS AND METHODS FOR SELECTIVE PROTEOLYSIS OF GLUCOCORTICOID RECEPTORS

This application claims the benefit of priority of U.S. Provisional Application No. 62/657,598, filed Apr. 13, 2018, the disclosure of which is hereby incorporated by reference as if written herein in its entirety.

Disclosed herein are steroidal glucocorticoid receptor (GR) ligands and related compositions that degrade the GR and/or modulate its activity that may be utilized as pharmaceuticals for the treatment of diseases including cancer. Methods to decrease the activity of glucocorticoid receptors in a human or animal subject are also provided for the treatment diseases such as cancer.

Castration resistant prostate cancer (CRPC) is a devastating disease with significant mortality and limited treatment options. Recently approved anti-androgen drugs such as enzalutamide show encouraging clinical activity against CRPC. Unfortunately, resistance develops within months of initiating therapy in most patients, ultimately resulting in mortality. Studies have shown that signaling through the glucocorticoid receptor (GR) is a primary mechanism of enzalutamide resistance. Furthermore, glucocorticoid receptor antagonism has been shown both to diminish the progression of CRPC in high GR expressing tumors, and to reverse prostate cancer resistance to docetaxel, a widely used chemotherapeutic for prostate cancer. Importantly, a clinical study has shown that GR expression is elevated in metastatic CRPC lesions, and that relapse patients with high GR expression have poor survival.

Taken together, these studies suggest that reduction in GR activity would likely improve the clinical outcome of CRPC patients. However, small-molecule antagonists of GR, such as RU-486, have partial agonist activity, leading to inadvertent activation of a subset of GR target genes, and thus severely limiting their anti-tumor efficacy. This underscores the need for new therapeutics that can abolish signaling through GR.

The limited success to date of small-molecule medicinal chemistry in the treatment of CRPC via the GR has prompted the development of an alternative modality of treatment: the selective in vivo destruction of the GR. Clearly, the wholesale loss of GR in a tumor would provide at least the same effect as inhibition of GR with a small-molecule therapeutic, with the additional benefit that the partial agonism, and subsequent genetic activation of RU-486, and potentially other small-molecule inhibitors, would be avoided.

Novel compounds and pharmaceutical compositions, certain of which have been found to modulate and/or degrade the glucocorticoid receptor have been discovered, together with methods of synthesizing and using the compounds including methods for the treatment of diseases mediated by the glucocorticoid receptor, in a patient by administering the compounds.

BRIEF DESCRIPTION OF THE DRAWINGS

FIG. 1 illustrates a western blot analysis of GR level in H1299 cells. Cells were treated with (a) Example 2, (b) Example 3, and (c) Example 4 in the presence of 10% FBS, according the described assay procedure. In each pair, the top frame shows GR, and the bottom frame shows β-actin. The panels illustrate the effect of compounds disclosed herein on degrading GR. DMSO is used as a control (i) and the Example concentration ranged from 1 nM (ii), 10 nM (iii), 100 nM (iv), 1000 nM (v), and 10,000 nM (vi).

FIG. 2 illustrates a clonogenic assay of PC3 cells grown in 6-wells, with compounds added at 3.3 μM (FIG. 2*a*) and 10 μM (FIG. 2*b*) concentration. For each of FIGS. 2*a* and 2*b*: (i) indicates DMSO control; (ii) indicates RU-486 (for GR antagonism); (iii) indicates enzalutamide (for AR antagonism); (iv) indicates Example 2; and (v) indicates Example 3.

FIG. 4 illustrates immunohistochemistry staining of GR in liver of mice treated with (a) vehicle or (b) Example 3 (66 mg/kg) intraperitoneally.

DETAILED DESCRIPTION

Figure 3:
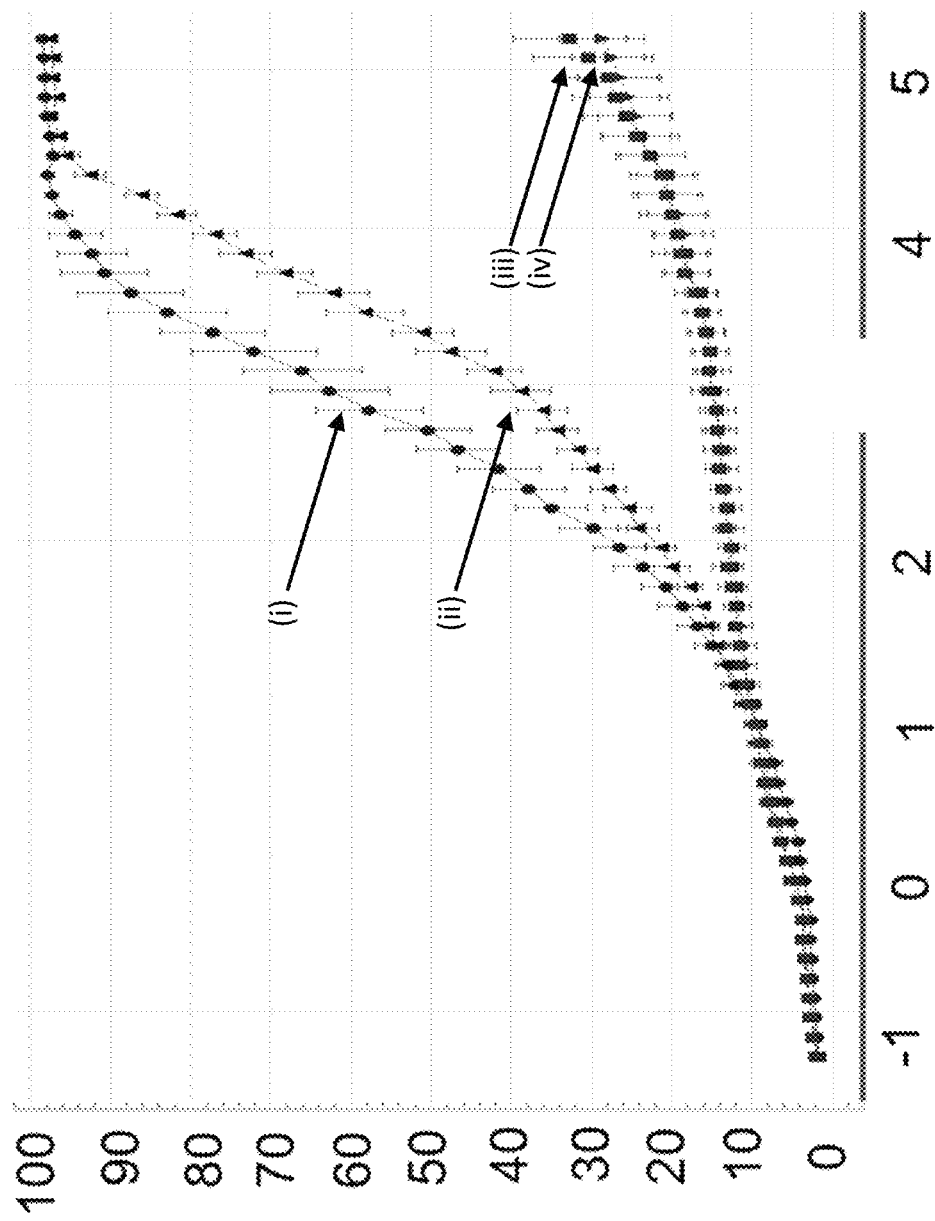
FIG. 3 illustrates a cell proliferation assay of DU145 cells with Example 3. Horizontal axis: time in days; vertical axis: confluency. DMSO control (i; ovals), 1 μM of Example 2 (ii, triangles), 3.3 μM of Example 2 (iii, squares), and 10 μM of Example 2 (iv, inverted triangles) were added on 96-well plated cells and proliferation followed for 5 days using Incucyte.

Disclosed herein are compounds that contain a steroidal moiety linked to a ubiquitin E3 ligase moiety. Without wishing to be bound by theory, it is theorized that the steroidal moiety will bind to the glucocorticoid receptor, and the presence of the E3 ligase moiety will promote the ubiquitin/proteasome reaction cascade that will ultimately lead to the degradation of the glucocorticoid receptor.

In certain embodiments of the present disclosure, compounds have structural Formula I:

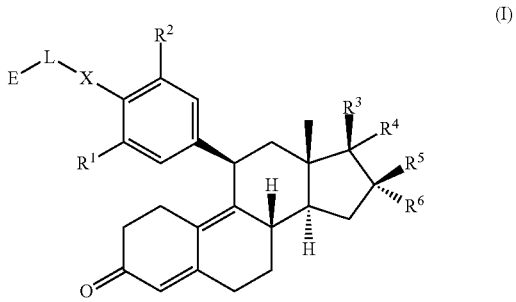

(I)

or a salt thereof, wherein:
E is an E3 ligase ligand;
L is chosen from *—$(CH_2)_nCH_2N(R^7)CO(CH_2)_p$ $CH_2$—**, *—$CO(CH_2)_nCH_2$—**, *—$CO(CH_2)_qO$ $(CH_2CH_2O)_nCH_2(CH_2)_p$—**, *—$(CH_2)_nCH_2$—**, *—$(CH_2)_qO(CH_2CH_2O)_nCH_2(CH_2)_p$—**,

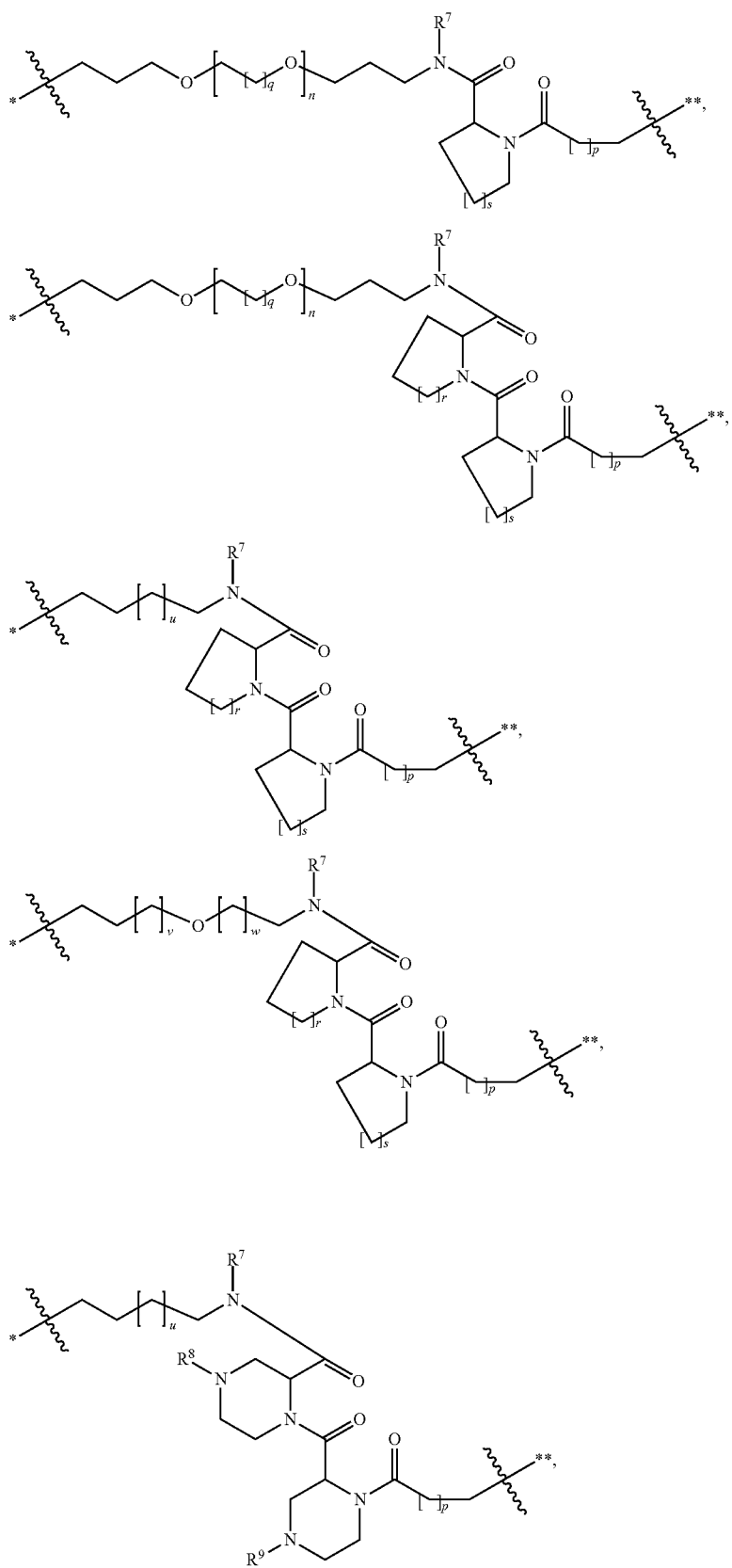

-continued

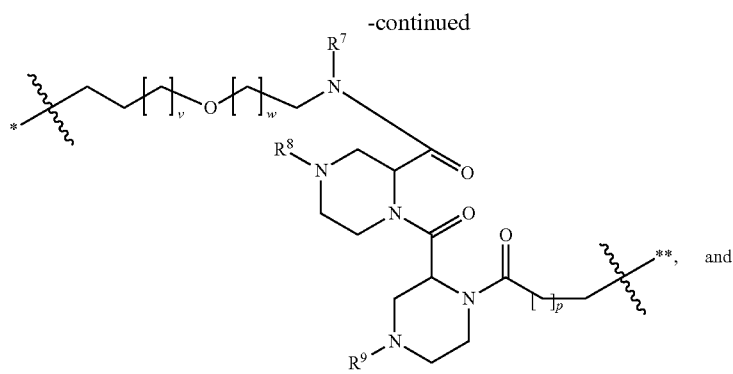

and

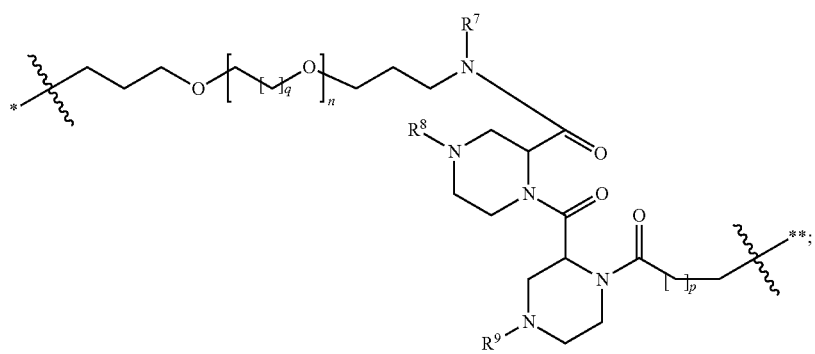

represents the point of attachment to E;
** represents the point of attachment to X;
X is chosen from O, $NR^{10}$, S, SO, and $SO_2$;
$R^1$ and $R^2$ are independently chosen from H, alkyl, cycloalkyl, heterocycloalkyl, aryl, heteroaryl, alkoxy, alkenyl, alkynyl, halo, alkylamino, dialkylamino, cyano, and hydroxy;
$R^3$ and $R^4$ are independently chosen from H, alkyl, alkoxy, alkenyl, alkylnyl, and hydroxyl, or
  $R^3$ and $R^4$, together with the atom to which they are attached, form a cycloalkyl or heterocycloalkyl ring, either of which is optionally substituted with 1, 2, or 3 $R^{11}$ groups;
$R^5$ and $R^6$ are independently chosen from H, alkyl, haloalkyl, alkoxy, amino, alkylamino, dialkylamino, cycloalkyl, (cycloalkyl)alkyl, heterocycloalkyl, (heterocycloalkyl)alkyl, $CONHR^{12}R^{13}$, $SO_2NHR^{12}R^{13}$, $SOR^{14}$, $SO_2R^{14}$, halo, hydroxy, and cyano, or
  $R^5$ and $R^6$, together with the atom to which they are attached, form a cycloalkyl or heterocycloalkyl ring, either of which is optionally substituted with 1, 2, or 3 $R^{15}$ groups;
$R^7$ is chosen from H, alkyl, cycloalkyl, (cycloalkyl)alkyl, $(CH_2)_t COOH$, alkylcarbonyl, and $—CO(CH_2)_t COOH$;
$R^8$ and $R^9$ are independently chosen from H, alkyl, alkylcarbonyl, cycloalkylcarbonyl, alkoxycarbonyl, alkylsulfonyl, $—(CH_2)_t COOH$, $—CO(CH_2)_t COOH$, $—COO(CH_2)_t COOH$, and $—(CH_2)_t SO_2OH$.
$R^{10}$ is chosen from H, alkyl, alkoxyalkyl, cycloalkyl, and heterocycloalkyl;
each $R^{11}$ is independently chosen from alkyl, cycloalkyl, heterocycloalkyl, alkoxy, cyano, halo, and hydroxy;
each $R^{12}$ and $R^{13}$ is independently chosen from alkyl, cycloalkyl, and heterocycloalkyl;

each $R^{14}$ is independently chosen from alkyl, cycloalkyl, and heterocycloalkyl;
each $R^{15}$ is independently chosen from alkyl, cycloalkyl, heterocycloalkyl, alkoxy, cyano, halo, and hydroxy;
n and p are independently chosen from 0-11, inclusive;
q is chosen from 0-11, inclusive;
r and s are independently chosen from 1-4, inclusive;
t is chosen from 1-8, inclusive;
u is chosen from 0-16, inclusive; and
v and w are independently chosen from 0-8, inclusive.

Certain compounds disclosed herein may possess useful activity for modulating or degrading the glucocorticoid receptor, and may be used in the treatment or prophylaxis of a disease or condition in which the glucocorticoid receptor plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating or degrading the glucocorticoid receptor. Other embodiments provide methods for treating a disorder mediated by the glucocorticoid receptor in a patient in need of such treatment, comprising administering to said patient a therapeutically effective amount of a compound or composition according to the present disclosure. Also provided is the use of certain compounds disclosed herein for use in the manufacture of a medicament for the treatment of a disease or condition ameliorated by the degradation or modulation of the glucocorticoid receptor.

In certain embodiments, E is chosen from

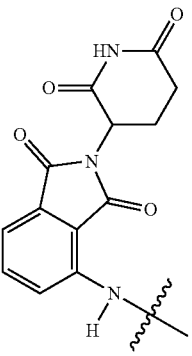

and

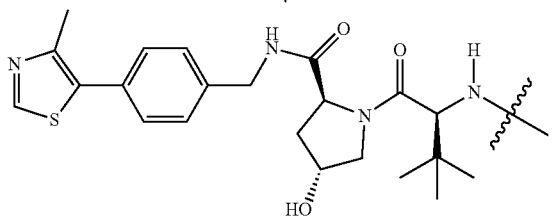

In certain embodiments,
L is chosen from *—(CH$_2$)$_n$CH$_2$N(R$^7$)CO(CH$_2$)$_p$CH$_2$—**, *—CO(CH$_2$)$_n$CH$_2$—**, *—CO(CH$_2$)$_q$O(CH$_2$CH$_2$O)$_n$CH$_2$(CH$_2$)$_p$—**, *—(CH$_2$)$_n$CH$_2$—**, *—(CH$_2$)$_q$O(CH$_2$CH$_2$O)$_n$CH$_2$(CH$_2$)$_p$—**,

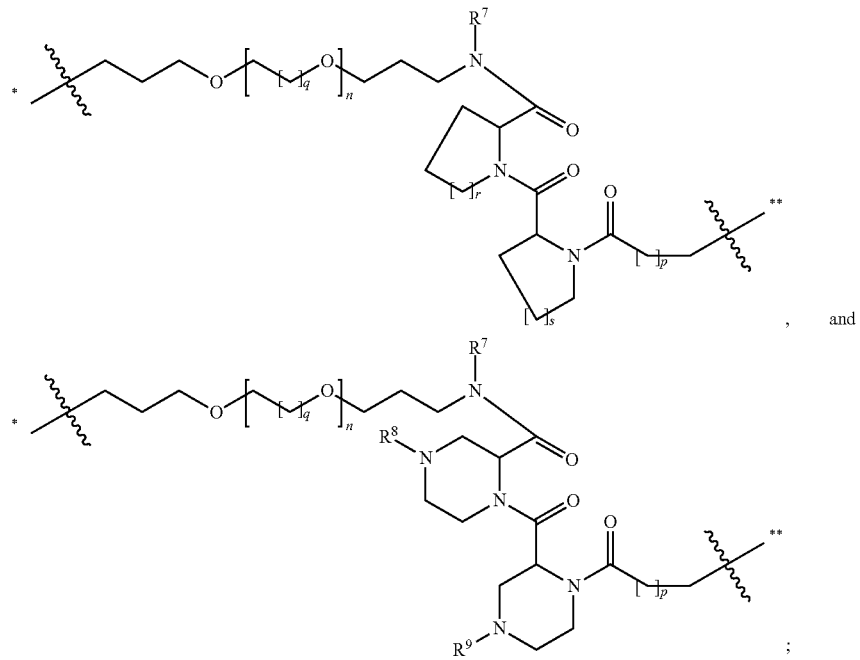

* represents the point of attachment to E;
** represents the point of attachment to X;
n and p are independently chosen from 0-11, inclusive;
q is chosen from 0-11, inclusive;
r and s are independently chosen from 1-4, inclusive; and
t is chosen from 1-8, inclusive.

In certain embodiments, n and p are independently chosen from 0-11, inclusive; and q is chosen from 0-3, inclusive.

In certain embodiments, n and p are independently chosen from 0-3, inclusive; and q is chosen from 0-11, inclusive.

In certain embodiments, X is chosen from O and NR$^{10}$.

In certain embodiments, X is N(CH$_3$).

In certain embodiments, R$^1$ and R$^2$ are independently chosen from H, alkyl, cycloalkyl, heterocycloalkyl, aryl, heteroaryl, alkoxy, halo, alkylamino, dialkylamino, cyano, and hydroxy.

In certain embodiments, R$^1$ and R$^2$ are independently chosen from H, alkyl, cycloalkyl, alkoxy, halo, alkylamino, dialkylamino, cyano, and hydroxy.

In certain embodiments, R$^3$ and R$^4$ are independently chosen from H, alkyl, alkoxy, alkenyl, alkylnyl, and hydroxyl.

In certain embodiments, R$^3$ and R$^4$ are independently chosen from H, alkyl, alkoxy, alkenyl, alkylnyl, and hydroxyl.

In certain embodiments, R$^3$ and R$^4$ are independently chosen from H, alkyl, alkoxy, —CH=CH(alkyl), —C≡C(alkyl), and hydroxyl.

In certain embodiments, at least one of R$^3$ and R$^4$ is hydroxy.

In certain embodiments, at least one of R$^3$ and R$^4$ is chosen from alkenyl and alkylnyl.

In certain embodiments, at least one of R$^3$ and R$^4$ is alkylnyl.

In certain embodiments, at least one of R$^3$ and R$^4$ is chosen from —CH=CH(alkyl) and —C≡C(alkyl).

In certain embodiments, at least one of R$^3$ and R$^4$ is —C≡C(alkyl).

In certain embodiments, R$^3$ and R$^4$, together with the atom to which they are attached, form a cycloalkyl ring which is optionally substituted with 1 or 2 R$^{11}$ groups.

In certain embodiments, R$^3$ and R$^4$, together with the atom to which they are attached, form a heterocycloalkyl ring which is optionally substituted with 1 or 2 R$^{11}$ groups.

In certain embodiments, R$^3$ and R$^4$, together with the atom to which they are attached, form a heterocycloalkyl ring which is optionally substituted with 1 or 2 $R^{11}$ groups, and which contains 1 or 2 groups selected from —O—, —NH—, —S—, —SO—, and —SO$_2$—.

In certain embodiments, $R^3$ and $R^4$, together with the atom to which they are attached, form a cycloalkyl or heterocycloalkyl ring.

In certain embodiments, at least one of $R^5$ and $R^6$ is H.

In certain embodiments, $R^5$ and $R^6$ are independently chosen from H, alkyl, haloalkyl, alkoxy, amino, alkylamino, dialkylamino, cycloalkyl, (cycloalkyl)alkyl, heterocycloalkyl, (heterocycloalkyl)alkyl, $CONHR^{12}R^{13}$, $SO_2NHR^{12}R^{13}$, $SOR^{14}$, $SO_2R^{14}$, halo, hydroxy, and cyano.

In certain embodiments, $R^5$ and $R^6$, together with the atom to which they are attached, form a cycloalkyl ring, which is optionally substituted with 1 or 2 $R^{15}$ groups.

In certain embodiments, $R^5$ and $R^6$, together with the atom to which they are attached, form a heterocycloalkyl ring, which is optionally substituted with 1 or 2 $R^{15}$ groups.

In certain embodiments, $R^5$ and $R^6$, together with the atom to which they are attached, form a heterocycloalkyl ring, which is optionally substituted with 1 or 2 $R^{15}$ groups, and which contains 1 or 2 groups selected from —O—, —NH—, —S—, —SO—, and —SO$_2$—.

In certain embodiments, $R^5$ and $R^6$, together with the atom to which they are attached, form a cycloalkyl or heterocycloalkyl ring.

In certain embodiments, $R^7$ is chosen from H, alkyl, and cycloalkyl.

In certain embodiments, $R^8$ and $R^9$ are independently chosen from H, alkyl, alkylcarbonyl, cycloalkylcarbonyl, and alkoxycarbonyl.

In certain embodiments, $R^{10}$ is chosen from H, alkyl, and cycloalkyl.

In certain embodiments, the compounds have structural Formula II:

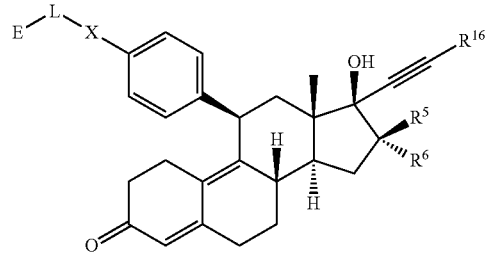

(II)

E is an E3 ligase ligand;
L is chosen from *—(CH$_2$)$_n$CH$_2$N(R$^7$)CO(CH$_2$)$_p$CH$_2$—**, *—CO(CH$_2$)$_n$CH$_2$—**, *—CO(CH$_2$)$_q$O(CH$_2$CH$_2$O)$_n$CH$_2$(CH$_2$)$_p$—**,

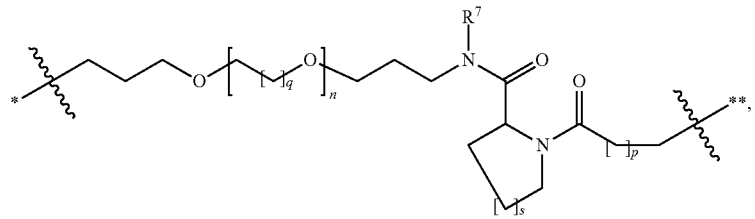

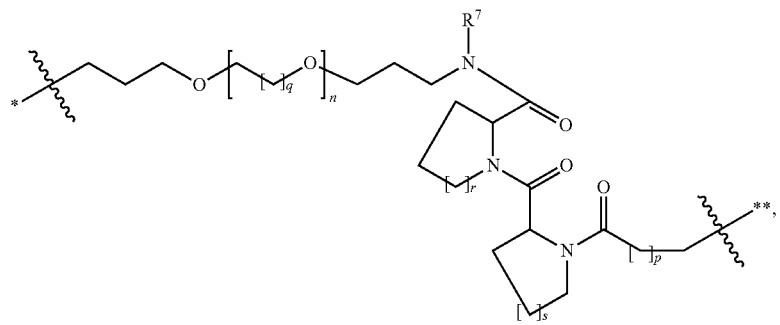

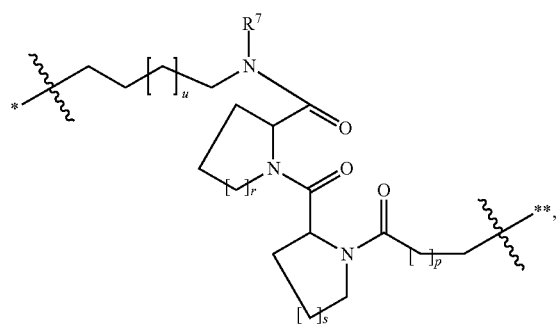

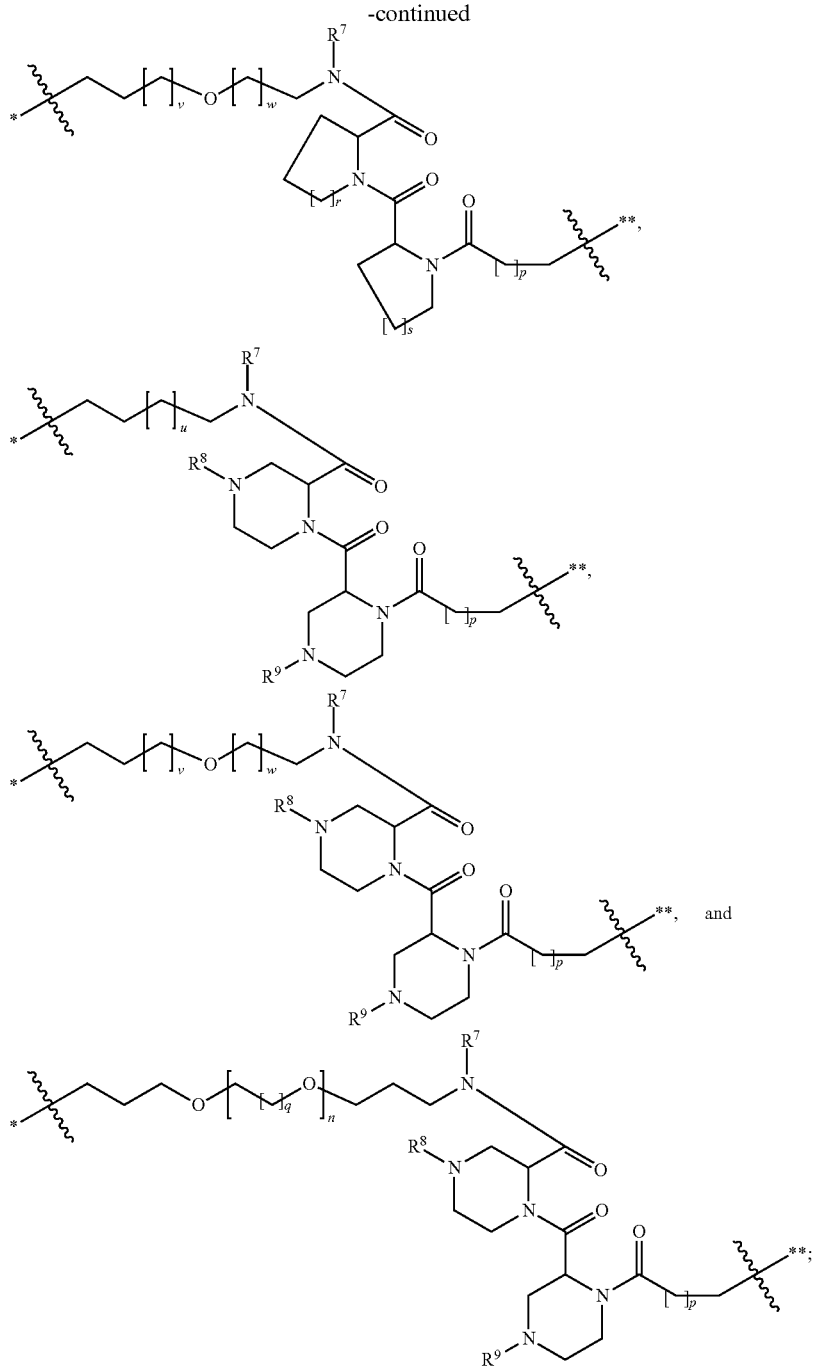

* represents the point of attachment to E;
** represents the point of attachment to X;
X is chosen from O, $NR^{10}$, S, SO, and $SO_2$;
$R^1$ and $R^2$ are independently chosen from H, alkyl, cycloalkyl, heterocycloalkyl, aryl, heteroaryl, alkoxy, alkenyl, alkynyl, halo, alkylamino, dialkylamino, cyano, and hydroxy;
$R^5$ and $R^6$ are independently chosen from H, alkyl, haloalkyl, alkoxy, amino, alkylamino, dialkylamino, cycloalkyl, (cycloalkyl)alkyl, heterocycloalkyl, (heterocycloalkyl)alkyl, $CONR^{12}R^{13}$, $SO_2NR^{12}R^{13}$, $SOR^{14}$, $SO_2R^{14}$, halo, hydroxy, and cyano, or $R^5$ and $R^6$, together with the atom to which they are attached, form a cycloalkyl or heterocycloalkyl ring, either of which is optionally substituted with 1, 2, or 3 $R^{15}$ groups;

$R^7$ is chosen from H, alkyl, cycloalkyl, (cycloalkyl)alkyl, $(CH_2)_tCOOH$, alkylcarbonyl, and $-CO(CH_2)_tCOOH$;

$R^8$ and $R^9$ are independently chosen from H, alkyl, alkylcarbonyl, cycloalkylcarbonyl, alkoxycarbonyl, alkylsulfonyl, $-(CH_2)_tCOOH$, $-CO(CH_2)_tCOOH$, $-COO(CH_2)_tCOOH$, and $-(CH_2)_tSO_2OH$.

$R^{10}$ is chosen from H, alkyl, alkoxyalkyl, cycloalkyl, and heterocycloalkyl;

each $R^{11}$ is independently chosen from alkyl, cycloalkyl, heterocycloalkyl, alkoxy, cyano, halo, and hydroxy;

each $R^{12}$ and $R^{13}$ is independently chosen from H, alkyl, cycloalkyl, and heterocycloalkyl;

each $R^{14}$ is independently chosen from alkyl, cycloalkyl, and heterocycloalkyl;

each $R^{15}$ is independently chosen from alkyl, cycloalkyl, heterocycloalkyl, alkoxy, cyano, halo, and hydroxy;

$R^{16}$ is chosen from H and alkyl;

n and p are independently chosen from 0-11, inclusive;

q is chosen from 0-11, inclusive;

r and s are independently chosen from 1-4, inclusive; and t is chosen from 1-8, inclusive.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present disclosure also relates to a method of inhibiting at least one glucocorticoid receptor function comprising the step of contacting the glucocorticoid receptor with a compound as described herein. The cell phenotype, cell proliferation, activity of the glucocorticoid receptor, change in biochemical output produced by active glucocorticoid receptor, expression of the glucocorticoid receptor, or binding of the glucocorticoid receptor with a natural binding partner may be monitored. Such methods may be modes of treatment of disease, biological assays, cellular assays, biochemical assays, or the like.

The present disclosure also relates to a method of degrading the glucocorticoid receptor comprising the step of contacting the glucocorticoid receptor with a compound as described herein. The cell phenotype, cell proliferation, activity of the glucocorticoid receptor, change in biochemical output produced by active glucocorticoid receptor, expression of the glucocorticoid receptor, or binding of the glucocorticoid receptor with a natural binding partner may be monitored. Such methods may be modes of treatment of disease, biological assays, cellular assays, biochemical assays, or the like.

Also provided herein is a method of treatment of a glucocorticoid receptor-mediated disease comprising the administration of a therapeutically effective amount of a compound as disclosed herein, or a salt thereof, to a patient in need thereof.

In certain embodiments, the disease is cancer.

In certain embodiments, the cancer is chosen from prostate cancer, breast cancer, ovarian cancer, and endometrial cancer.

In certain embodiments, the cancer is castration resistant prostate cancer

In certain embodiments, the cancer is triple negative breast cancer.

Also provided herein is a compound as disclosed herein for use as a medicament.

Also provided herein is a compound as disclosed herein for use as a medicament for the treatment of a glucocorticoid receptor-mediated disease.

Also provided is the use of a compound as disclosed herein as a medicament.

Also provided is the use of a compound as disclosed herein as a medicament for the treatment of a glucocorticoid receptor-mediated disease.

Also provided is a compound as disclosed herein for use in the manufacture of a medicament for the treatment of a glucocorticoid receptor-mediated disease.

Also provided is the use of a compound as disclosed herein for the treatment of a glucocorticoid receptor-mediated disease.

Also provided herein is a method of inhibition of the glucocorticoid receptor comprising contacting the glucocorticoid receptor with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

Also provided is a method of modulation of a glucocorticoid receptor-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the oral pharmaceutical composition is chosen from a tablet and a capsule.

Abbreviations and Definitions

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group.

Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzindolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, C(O)$CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"Glucocorticoid receptor antagonist" is used herein to refer to a compound that exhibits an EC50 with respect to the glucocorticoid receptor activity of no more than about 100 μM and more typically not more than about 50 μM, as measured in the glucocorticoid receptor (assay name) described generally herein. "EC50" is that concentration of antagonist which reduces the activity of an enzyme (e.g., the glucocorticoid receptor) to half-maximal level. Certain compounds disclosed herein have been discovered to exhibit inhibition activity against the glucocorticoid receptor. In certain embodiments, compounds will exhibit an EC50 with respect to the glucocorticoid receptor of no more than about 10 μM; in further embodiments, compounds will exhibit an EC50 with respect to the glucocorticoid receptor of no more than about 2 μM; in yet further embodiments, compounds will exhibit an EC50 with respect to the glucocorticoid receptor of not more than about 200 nM; in yet further embodiments, compounds will exhibit an EC50 with respect to the glucocorticoid receptor of not more than about 50 nM, as measured in the glucocorticoid receptor assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the disclosure may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combinations and Combination Therapy

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the disclosure with: Abiraterone Acetate, Apalutamide, Bicalutamide, Cabazitaxel, Casodex (Bicalutamide), Degarelix, Docetaxel, Enzalutamide, Erleada (Apalutamide), Flutamide, Goserelin Acetate, Jevtana (Cabazitaxel), Leuprolide Acetate, Lupron (Leuprolide Acetate), Lupron Depot (Leuprolide Acetate), Lupron Depot-Ped (Leuprolide Acetate), Mitoxantrone Hydrochloride, Nilandron (Nilutamide), Nilutamide, Provenge (Sipuleucel-T), Radium 223 Dichloride, Sipuleucel-T, Taxotere (Docetaxel), Viadur (Leuprolide Acetate), Xofigo (Radium 223 Dichloride), Xtandi (Enzalutamide), Zoladex (Goserelin Acetate), and Zytiga (Abiraterone Acetate).

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Indications for Use and Treatment

Thus, in another aspect, certain embodiments provide method of inhibition of the glucocorticoid receptor comprising contacting the glucocorticoid receptor with a compound as disclosed herein.

Thus, in another aspect, certain embodiments provide method of degradation of the glucocorticoid receptor comprising contacting the glucocorticoid receptor with a compound as disclosed herein.

In certain embodiments, said degradation is selective for the glucocorticoid receptor as compared to other nuclear receptors.

In certain embodiments, said degradation does not decrease at elevated levels of said compound.

In another aspect, certain embodiments provide methods for treating glucocorticoid receptor-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of glucocorticoid receptor-mediated disorders.

In certain embodiments, the diseases to be treated by the compounds, compositions, and methods disclosed herein include inflammation, tissue rejection, auto-immunity, cancer including leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome.

In certain embodiments, said disease is cancer.

In certain embodiments, said cancer is characterized by high expression of the glucocorticoid receptor.

In certain embodiments, said cancer is chosen from prostate cancer, breast cancer, ovarian cancer, and endometrial cancer.

In certain embodiments, said cancer is prostate cancer.

In certain embodiments, prostate cancer is castration resistant prostate cancer.

cancer is breast cancer.

In certain embodiments, said breast cancer is triple negative breast cancer.

In certain embodiments, said cancer is ovarian cancer.

In certain embodiments, said cancer is endometrial cancer.

Also provided is a method for treating cancer with a reduced incidence of one or more side effects in a patient comprising the administration of a therapeutically effective amount of a compound as disclosed herein to a patient, wherein the effect is chosen from weight loss, loss of appetite, anemia, bone pain, neurologic defects from spinal cord compression, lower extremity pain, and lower extremity edema.

In certain embodiments, the therapeutically effective amount of the compound is not limited by competition of the ligand for ternary complex formation.

In certain embodiments, the diseases to be treated by the compounds, compositions, and methods disclosed herein are inflammatory diseases.

In certain embodiments, the inflammatory diseases include inflammatory bowel disease, systemic lupus erythematosus, polyarteritis nodosa, Wegener's granulomatosis, giant cell arteritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, juvenile rheumatoid arthritis, juvenile idiopathic arthritis, ankylosing spondylitis, psoriasis, plaque psoriasis, and psoriatic arthritis.

In certain embodiments, the compounds, compositions, and methods disclosed herein can be used as immunostimulants and repressors, and as wound healing and tissue repair agents.

In certain embodiments, the diseases to be treated by the compounds, compositions, and methods disclosed herein are topical diseases.

In certain embodiments, the topical diseases include inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma and ocular diseases.

In certain embodiments, the compounds, compositions, and methods disclosed herein can be used to treat disease states associated with human immunodeficiency virus (HIV), cell apoptosis, and cancer.

In certain embodiments, the disease states associated with human immunodeficiency virus (HIV), cell apoptosis, and cancer include Kaposi's sarcoma, immune system activation and modulation, desensitization of inflammatory responses, IL-1 expression, anti-retroviral therapy, natural killer cell development, lymphocytic leukemia, and treatment of retinitis pigmentosa.

In certain embodiments, the compounds, compositions, and methods disclosed herein can be used to treat disease states associated with cognitive and behavioral processes.

In certain embodiments, the cognitive and behavioral processes include cognitive performance, memory and learning enhancement, depression, addiction, mood disorders, chronic fatigue syndrome, schizophrenia, stroke, sleep disorders, and anxiety.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

List of Abbreviations $Ac_2O$=acetic anhydride; AcCl=acetyl chloride; AcOH=acetic acid; AIBN=azobisisobutyronitrile; aq.=aqueous; $Bu_3SnH$=tributyltin hydride; $CD_3OD$=deuterated methanol; $CDCl_3$=deuterated chloroform; CDI=1,1'-Carbonyldiimidazole; DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; EDC.HCl=EDCI.HCl=1-ethyl-3-(3-dimethylaminopropyl)carbodiimide hydrochloride; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; i-PrOH=isopropanol; LAH=lithium aluminium hydride; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chlorosuccinimide; NMP=N-Methyl-2-pyrrolidone; $Pd(Ph_3)_4$=tetrakis(triphenylphosphine)palladium(0); $Pd_2(dba)_3$=tris(dibenzylideneacetone)dipalladium(0); $PdCl_2(PPh_3)_2$=bis(triphenylphosphine)palladium(II) dichloride; PG=protecting group; prep-HPLC=preparative high-performance liquid chromatography; PyBop=(benzotriazol-1-yloxy)-tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TBS=TBDMS=tert-butyldimethylsilyl; TBSCl=TBDMSCl=tert-butyldimethylchlorosilane; TEA=Et₃N=triethylamine; TFA=trifluoroacetic acid; TFAA=trifluoroacetic anhydride; THF=tetrahydrofuran; Tot=toluene; TsCl=tosyl chloride; XPhos=2-dicyclohexylphosphino-2',4',6'-triisopropylbiphenyl.

General Synthetic Methods for Preparing Compounds

The following schemes can be used to practice the present disclosure.

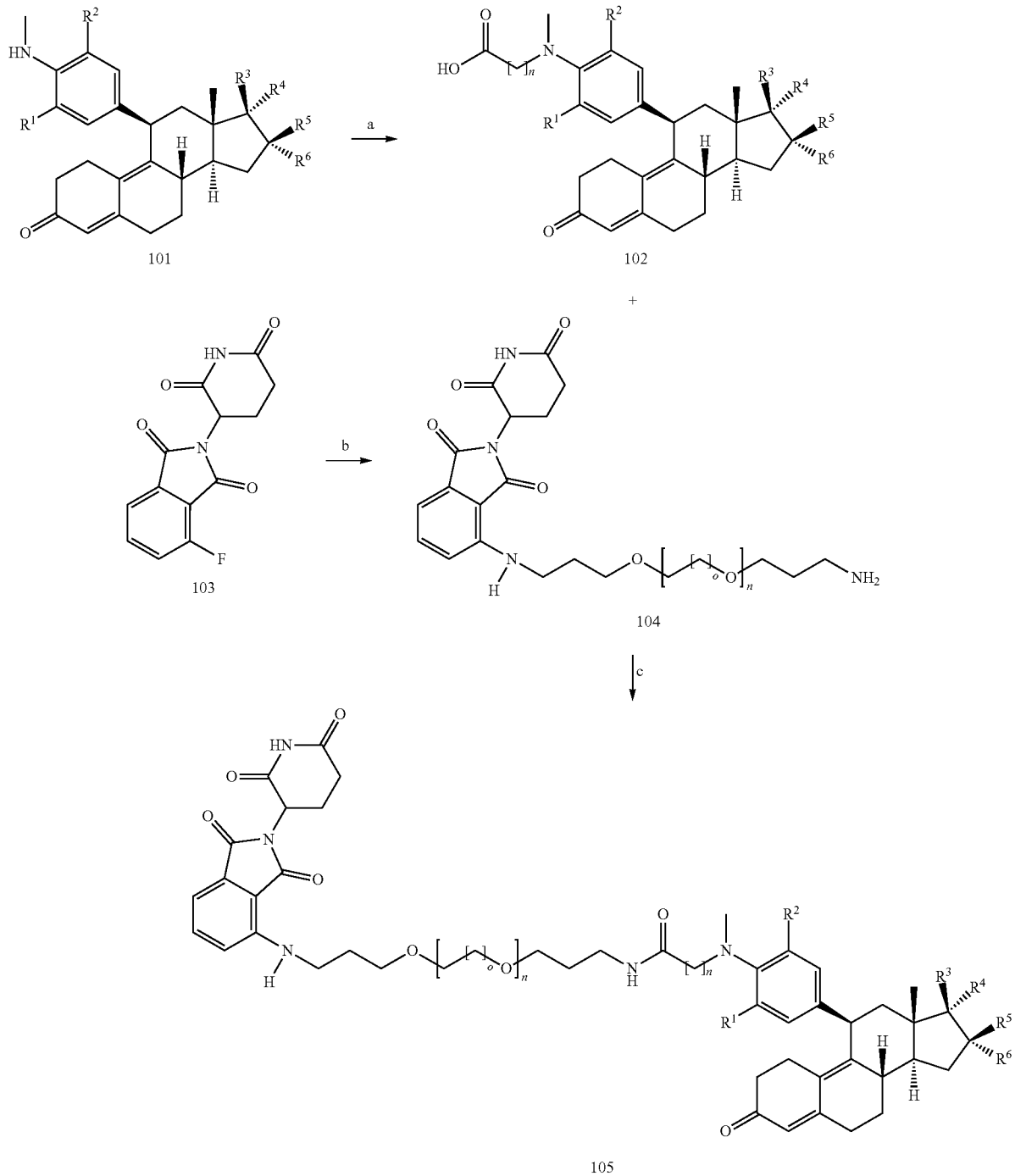

Examples 1-X can be synthesized using the following general synthetic procedure set forth in Scheme I. Anilines of general structure 101 are reacted with alkylating agents such as the haloalkane ester ethyl 4-iodobutanoate to give acids of structure 102 after hydrolysis. Amines 104 can be prepared from aryl fluoride 103 by reaction with a primary amine by mixing the two reagents in solvent with heat. The coupling of amines 104 with acids 102 provides amide compounds of the present disclosure of general structure 105.

Scheme II

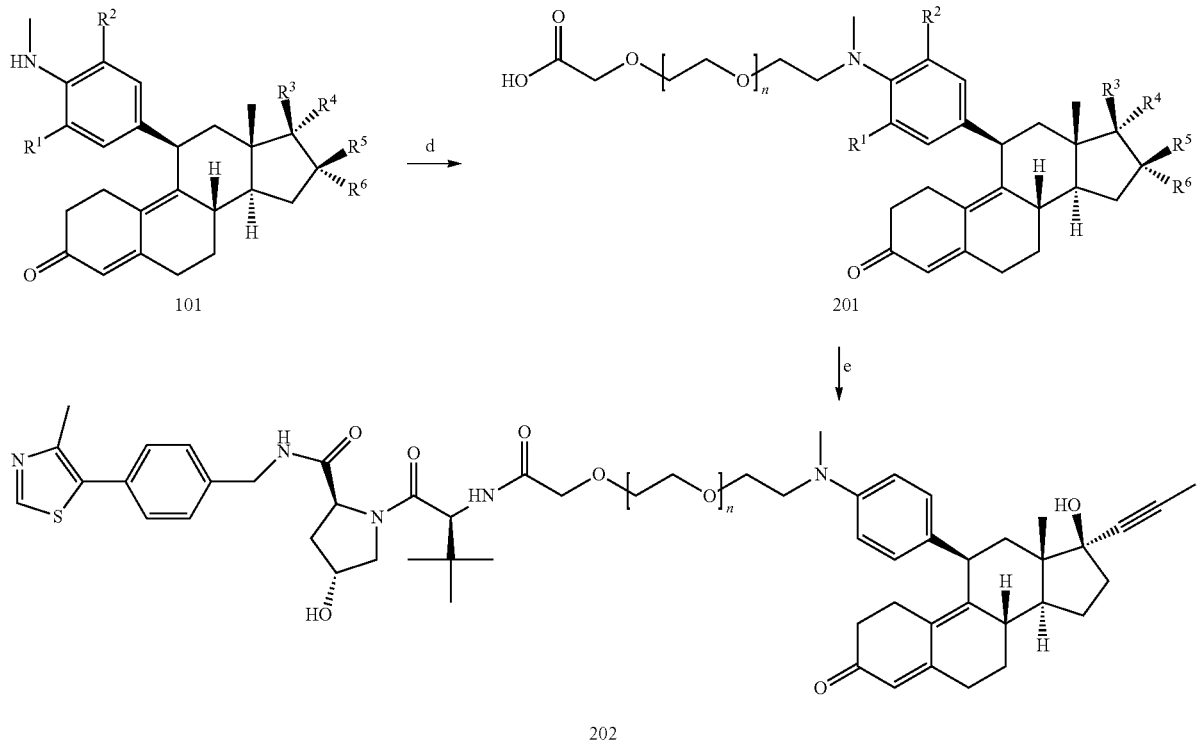

Examples Y-Z can be synthesized using the following general synthetic procedure set forth in Scheme II. Compound 201 can be obtained from 101 via alkylation with a ω-halo poly(oxyethylene) carboxylic ester, followed by hydrolysis of the ester functionality. Compounds of the present disclosure such as 202 can be prepared by coupling acid 201, using standard peptide coupling conditions, with E3 ligand amines like (2S,4R)-1-((S)-2-amino-3,3-dimethylbutanoyl)-4-hydroxy-N-(4-(4-methylthiazol-5-yl)benzyl)pyrrolidine-2-carboxamide.

Scheme III

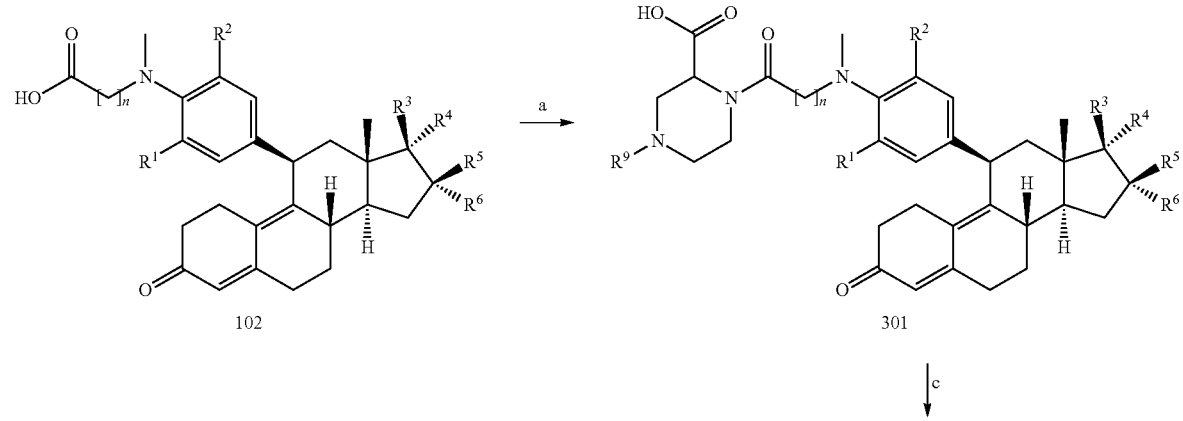

-continued

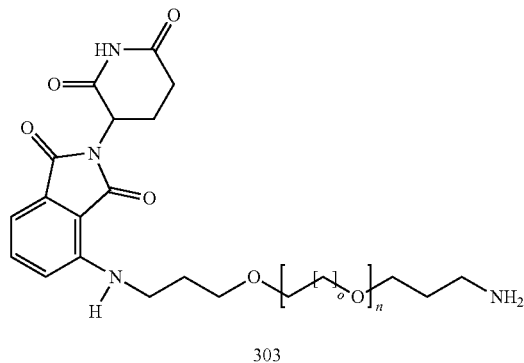

303

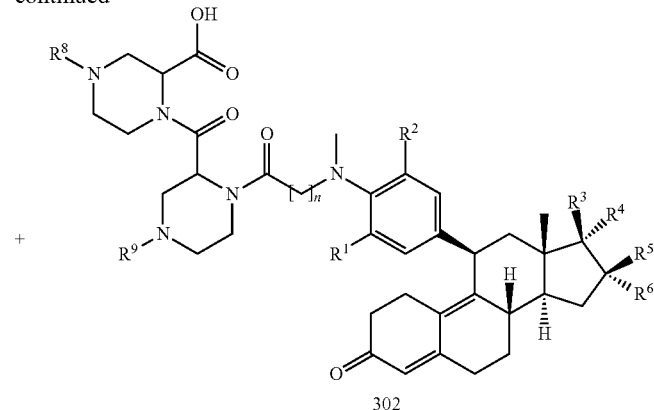

302

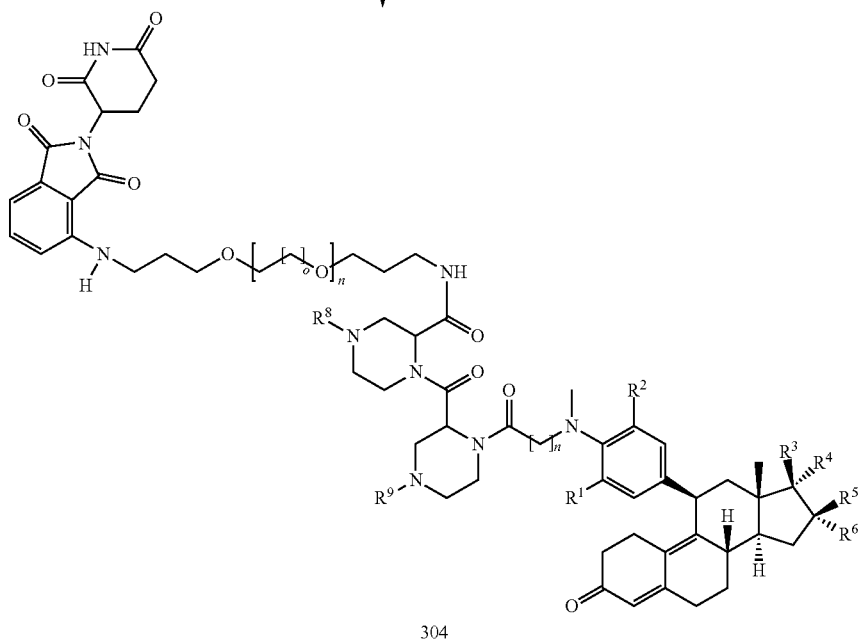

304

Examples Y-Z can be synthesized using the following general synthetic procedure set forth in Scheme III. Amino acid coupling of acids 102 and piperazine carboxylic esters such as 1-(tert-butyl) 3-methyl piperazine-1,3-dicarboxylate provides amides of general structure 301 after hydrolysis. A second coupling with a similar substrate can provide acids of general structure 302 after hydrolysis. A second amide coupling with amines of general structure 303 provides compounds of the present disclosure 304.

The following intermediates are used to prepare the compounds in this disclosure. All IUPAC names were generated using CambridgeSoft's ChemDraw.

Intermediate A

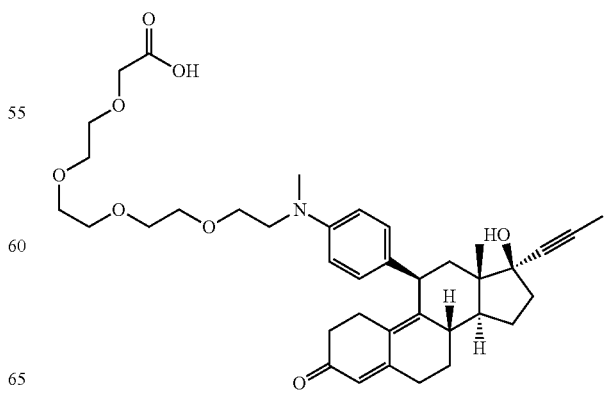

2-(4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)-5,8,11,14-tetraoxa-2-azahexadecan-16-oic acid

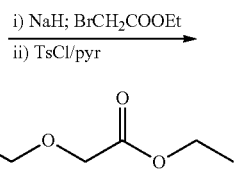

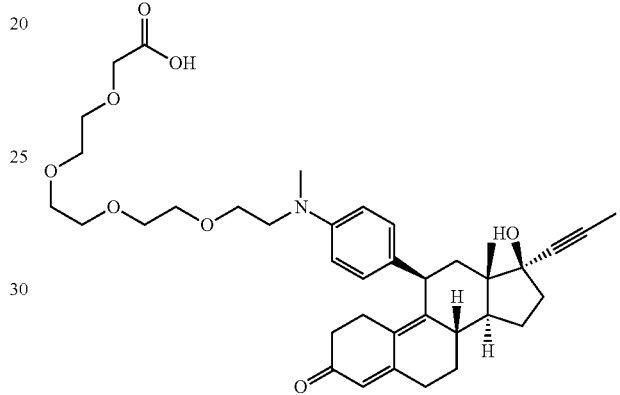

Ethyl 14-(p-toluenesulfonyloxy)-3,6,9,12-tetraoxa-tetradecanoate

To a solution of 2,2'-((oxybis(ethane-2,1-diyl))bis(oxy)) diethanol (1 ml, 5.79 mmol) in THF (10 ml) at 0° C. was added NaH (0.232 g, 5.79 mmol). The reaction was stirred for 30 min at 0° C., then ethyl 2-bromoacetate (0.641 ml, 5.79 mmol) was added. The reaction was then allowed to slowly warm to rt over an hour and then stirred for 3 hours at rt. The crude reaction mixture was concentrated in vacuo and then redissolved in $CHCl_3$ and pyridine. The reaction mixture was then treated with p-toluenesulfonyl chloride (how much?). and stirred at room temperature for 4 hours. The reaction mixture was diluted with EtOAc, $H_2O$ was added, and the layers were separated. The aqueous phase was extracted with EtOAc (3), the combined organic layers were washed with sat NaCl, dried over $Na_2SO_4$, filtered and concentrated under reduced pressure. The residue was purified via flash chromatography (20-70% EtOAc in hexanes) to give the title compound as a colorless oil in low yield (<10%). The compound was greater than 95% pure by reverse phase HPLC-MS with UV/vis and MS detection with a molecular ion of? (M+Na=457).

$^1$H-NMR (600 MHz, $CDCl_3$) δ 7.75 (dd, J=7.5, 1.5 Hz, 2H), 7.35 (dd, J=7.5, 1.5 Hz, 2H), 4.33 (s, 2H), 4.21, (q, J=8 Hz, 2H), 3.70 (m, 16H), 2.43 (s, 3H), 1.23 (d, q, J=8 Hz, 3H).

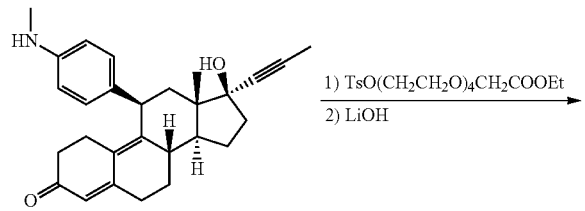

2-(4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)-5,8,11,14-tetraoxa-2-azahexadecan-16-oic acid To a solution of (8S,11R,13S,14S,17S)-17-hydroxy-13-methyl-11-(4-(methylamino)phenyl)-17-(prop-1-yn-1-yl)-6,7,8,11,12,13,14,15,16,17-decahydro-1H-cyclopenta[a]phenanthren-3(2H)-one (33.8 mg, 0.081 mmol) in $CH_3CN$ (0.2 ml) were added $iPr_2NEt$ (0.014 ml, 0.081 mmol), NaI, and the product from the previous step (35.3 mg, 0.081 mmol) and the resulting mixture was stirred at 82° C. for 2 h. The reaction was cooled to rt and concentrated in vacuo. The residue was purified by reverse phase preparative HPLC (Mobile phase: A=0.1% $TFA/H_2O$, B=0.1% TFA/MeCN; Gradient: B=10-90%; 20 min) to give 2-(4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)-5,8,11,14-tetraoxa-2-azahexadecan-16-oic acid as a tan solid. The product was dissolved in 0.4 mL of THF and 0.4 mL of water and treated with LiOH. The resulting mixture was stirred at room temperature for 2 hours. The residue was purified by reverse phase preparative HPLC (Mobile phase: A=0.1% $TFA/H_2O$, B=0.1% TFA/MeCN; Gradient: B=10-90%; 20 min) to give the title compound as a tan amorphous material. The compound was greater than 95% pure by reverse phase HPLC-MS with UV/vis and MS detection (M+H=650).

¹H-NMR (600 MHz, CDCl₃) δ 7.46 (dd, J=7.5, 1.5 Hz, 2H), 7.31 (dd, J=7.5, 1.5 Hz, 2H), 6.45 (s, 1H), 5.45 (s, 3H), 4.18 (m, 2H), 3.40 (m, 16H), 1.20-2.80 (m, 22H), 1.95 (s, 3H), 0.46 (s, 3H).

Intermediate B

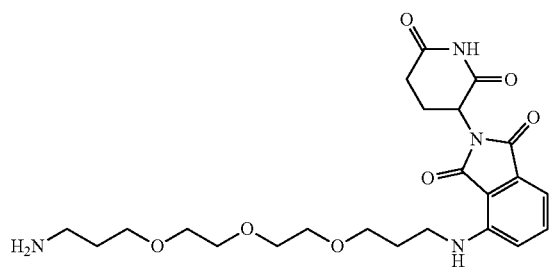 [SMILES: NCCCOCCOCCOCCCNc1cccc2c1C(=O)N(C1CCC(=O)NC1=O)C2=O]

4-((3-(2-(2-(3-Aminopropoxy)ethoxy)ethoxy)propyl)amino)-2-(2,6-dioxopiperidin-3-yl)isoindoline-1,3-dione tert-Butyl-(3-(2-(2-(3-((2-(2,6-dioxopiperidin-3-yl)-1,3-dioxoisoindolin-4-yl)amino)propoxy)ethoxy)ethoxy)propyl)carbamate To a suspension of 2-(2,6-dioxopiperidin-3-yl)-4-fluoroisoindoline-1,3-dione (B Zhou et al. "Discovery of a Small-Molecule Degrader of Bromodomain and Extra-Terminal (BET) Proteins with Picomolar Cellular Potencies and Capable of Achieving Tumor Regression J. Med. Chem. 2018, 61(2), 462-481, 652 mg, 2.360 mmol) in dioxane (10 ml) was added tert-butyl (3-(2-(2-(3-aminopropoxy)ethoxy)ethoxy)propyl)carbamate (770 mg, 2.403 mmol) and iPr₂NEt (0.5 ml, 2.86 mmol), and the resulting mixture was stirred at 90° C. for 24 h. LCMS showed no further progression. The dark reaction mixture was partitioned between EtOAc (200 mL) and water (200 mL) with brine added to aid in bi-layer formation. The organic layer was washed with brine, dried over Na₂SO₄, filtered and concentrated. The dark residue was purified via silica gel chromatography (2-5% MeOH in DCM). to give the title compound (584 mg, 1.013 mmol, 42.1% yield) as a yellow solid.

¹H-NMR (600 MHz, CDCl₃) δ 8.06 (s, 1H), 7.59 (dd, J=7.5, 7.5 Hz, 1H), 7.25 (dd, J=7.5, 1.5 Hz, 1H), 7.05 (s, 1H), 6.98 (dd, J=7.5, 1.5 Hz, 1H), 6.41 (s, 1H), 4.92 (t, 1H), 3.72 (m, 6H), 3.35 (m, 4H), 3.18 (M, 2H), 2.15 (m, 4H), 1.95 (m, 4H), 1.42 (s, 9H).

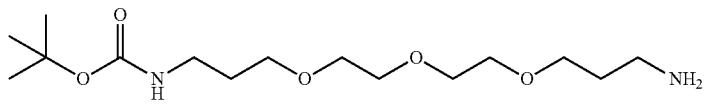

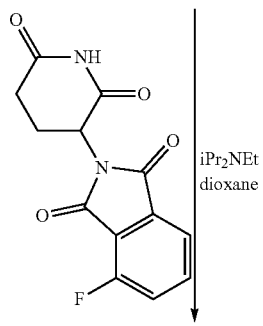

iPr₂NEt
dioxane

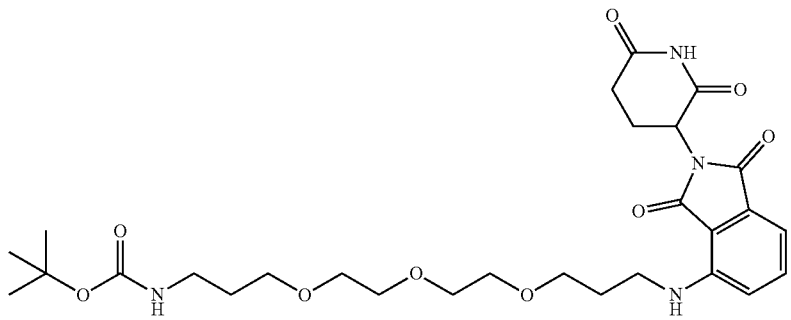

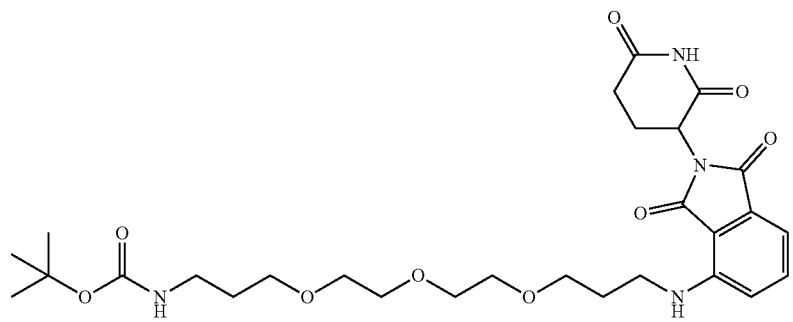

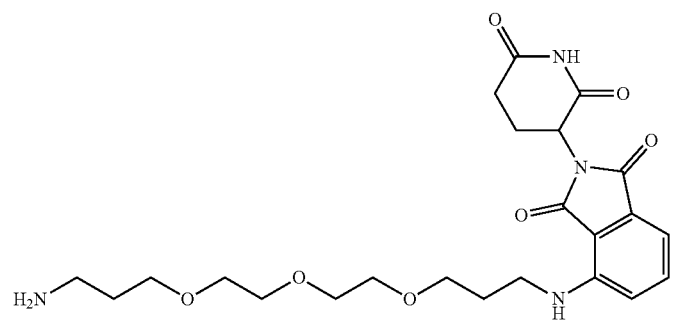

4-((3-(2-(2-(3-Aminopropoxy)ethoxy)ethoxy)propyl)amino)-2-(2,6-dioxopiperidin-3-yl)isoindoline-1,3-dione The product from the previous step (584 mg, 1.013 mmol) was treated with HCl (10 mL, 4M in dioxanes, 30.0 mmol) and the resulting mixture was stirred at RT for 6 hrs. Clean and complete de-protection observed after 6 hrs. The reaction mixture was concentrated, dissolved in acetonitrile/water (ca. 1:5, total 10 mL volume), froze, then lyophilized to give the title compound, as the hydrochloride salt (500 mg, 0.975 mmol, 96% yield) as a yellow amorphous material.

$^1$H-NMR (600 MHz, CDCl3) δ 9.18 (s, 1H), 7.49 (dd, J=7.5, 1H), 7.80 (s, 1H), 7.05 (dd, J=7.5, 7.5 Hz, 1H), 6.88 (dd, J=7.5, 1.5 Hz, 1H), 4.94 (dd, J=7 Hz, 3.52 (m, 8H), 3.31 (m, 2H), 3.15 (m, 2H), 2.71 (m, 6H), 2.15 (s, 2H), 1.95 (m, 6H).

$^{13}$C-NMR (600 MHz, CDCl$_3$) δ 171.9, 169.5, 167.9, 146.9, 137.2, 133.8, 117.3, 111.4, 109.8, 70.2, 69.9, 69.8, 69.4, 48.8, 40.6, 39.8, 31.33, 28.7, 26.4, 22.5.

Intermediate C

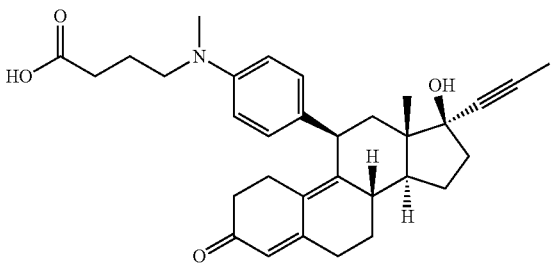

4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)-phenyl)(methyl)amino)butanoic acid

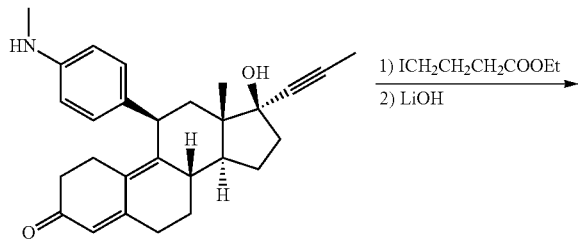

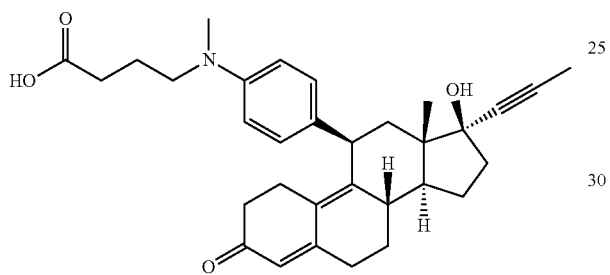

To a solution of (8S,11R,13S,14S,17S)-17-hydroxy-13-methyl-11-(4-(methylamino)phenyl)-17-(prop-1-yn-1-yl)-6,7,8,11,12,13,14,15,16,17-decahydro-1H-cyclopenta[a]phenanthren-3(2H)-one (Von Geldern, et al. "Liver-Selective Glucocorticoid Antagonists: A Novel Treatment for Type 2 Diabetes" *J. Med. Chem.*, 2004, 47 (17), 4213-4230) (100 mg, 0.241 mmol) in $CH_3CN$ (0.7 ml) was added $iPr_2NEt$ (0.046 ml, 0.265 mmol) and ethyl 4-iodobutanoate (0.042 ml, 0.241 mmol) and the resulting mixture was stirred at 82° C. for 12 h. The reaction was complete by analytical HPLC-MS and was cooled to room temperature and concentrated in vacuo. The crude products were dissolved in 2 mL of 1:1 $THF:H_2O$ and treated with LiOH. After 1 hour the reaction was complete by analytical HPLC MS. The crude product was removed by filtration and the residue was purified by reverse phase preparative HPLC (Mobile phase: A=0.1% $TFA/H_2O$, B=0.1% TFA/MeCN; Gradient: B=20-80%; 12 min) to give the title compound (110 mg, 0.219 mmol, 91% yield) as a tan solid. The compound was greater than 95% pure by reverse phase HPLC-MS with UV/vis and MS detection with a molecular ion of (M+H=502).

$^1$H-NMR (600 MHz, $CDCl_3$) δ 7.44 (dd, J=7.5, 1.5 Hz, 2H), 7.28 (dd, J=7.5, 1.5 Hz, 2H), 7.10 (s, 1H), 5.84 (s, 1H), 4.28 (s, 1H), 3.52 (m, 2H), 3.18 (s, 21H), 1.51-2.75 (m, 22H), 1.89 (s, 3H), 0.49 (s, 3H).

The disclosure is further illustrated by the following examples. All IUPAC names were generated using CambridgeSoft's ChemDraw.

Example 1

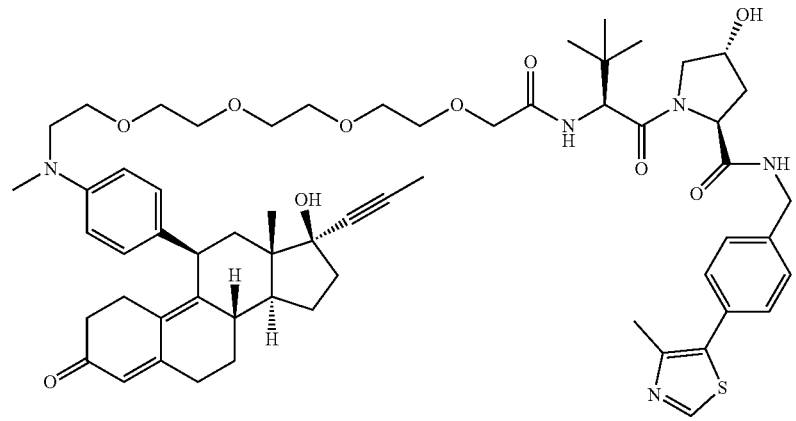

(2S,4R)-1-((S)-18-(tert-butyl)-2-(4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)-16-oxo-5,8,11,14-tetraoxa-2,17-diazanonadecan-19-oyl)-4-hydroxy-N-(4-(4-methylthiazol-5-yl)benzyl)pyrrolidine-2-carboxamide

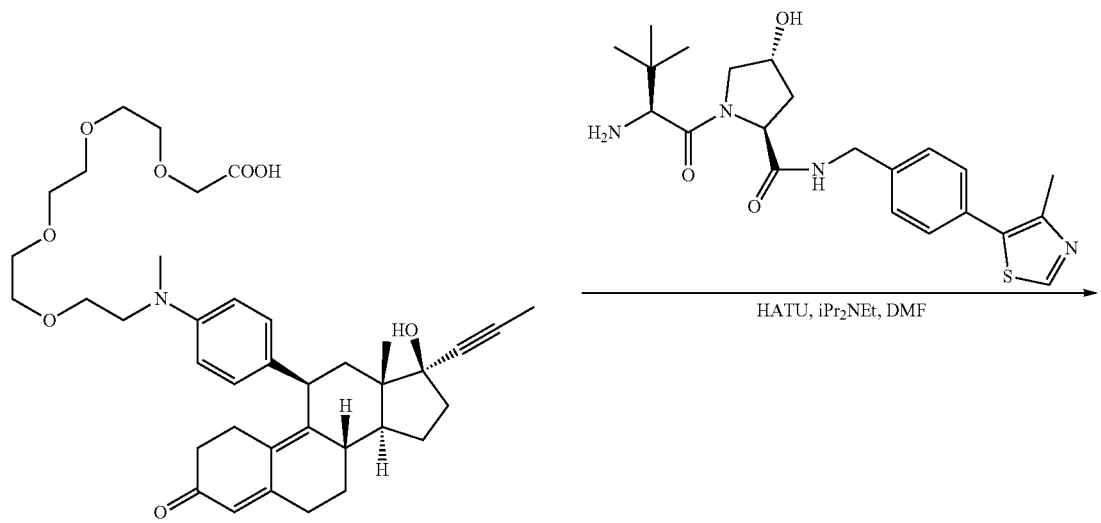

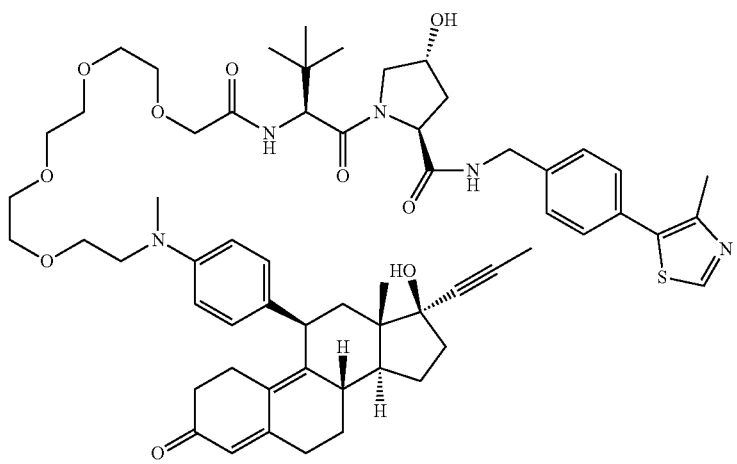

To a solution of Intermediate A and (2S,4R)-1-((S)-2-amino-3,3-dimethylbutanoyl)-4-hydroxy-N-(4-(4-methylthiazol-5-yl)benzyl)pyrrolidine-2-carboxamide (Crew and coworkers, "Identification and Characterization of Von Hippel-Lindau-Recruiting Proteolysis Targeting Chimeras (PROTACs) of TANK-Binding Kinase 1" J. Med. Chem 2018, 61(2), 583-598; 9.88 mg, 0.023 mmol) in DMF (0.2 ml) were added iPr$_2$NEt (7.63 μl, 0.044 mmol) and HATU (11.63 mg, 0.031 mmol) and the resulting mixture was stirred at room temperature for 12 h. The residue was purified by reverse phase preparative HPLC (Mobile phase: A=0.1% TFA/H$_2$O, B=0.1% TFA/MeCN; Gradient: B=10-90%; 20 min) to give the title compound (13.9 mg, 0.013 mmol, 59.9% yield) as a tan amorphous material. The compound was greater than 95% pure by reverse phase HPLC-MS with UV/vis and MS detection (M$^+$=1062).

$^1$H-NMR (600 MHz, CDCl$_3$) δ 9.37 (s, 1H), 7.40 (m, 8H), 5.88 (s, 1H), 4.80 (m, 10H), 4.07 (m, 1H), 3.52 (m, 19H), 1.40-2.75 (m, 28H), 1.01 (s, 9H), 0.98 (s, 3H).

Example 2
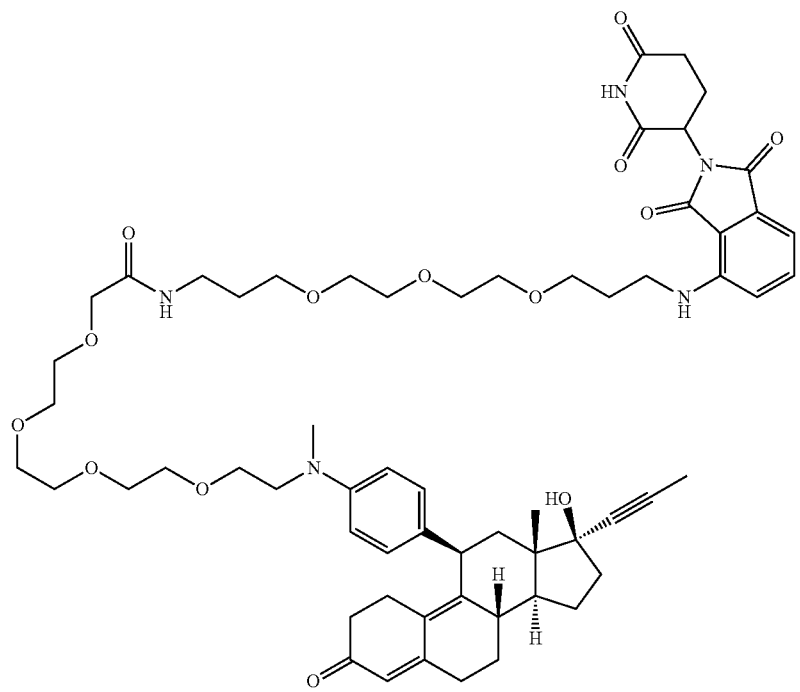
N-(3-(2-(2-(3-((2-(2,6-Dioxopiperidin-3-yl)-1,3-dioxoisoindolin-4-yl)amino)propoxy)-ethoxy)ethoxy)propyl)-2-(4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)-5,8,11,14-tetraoxa-2-azahexadecan-16-amide
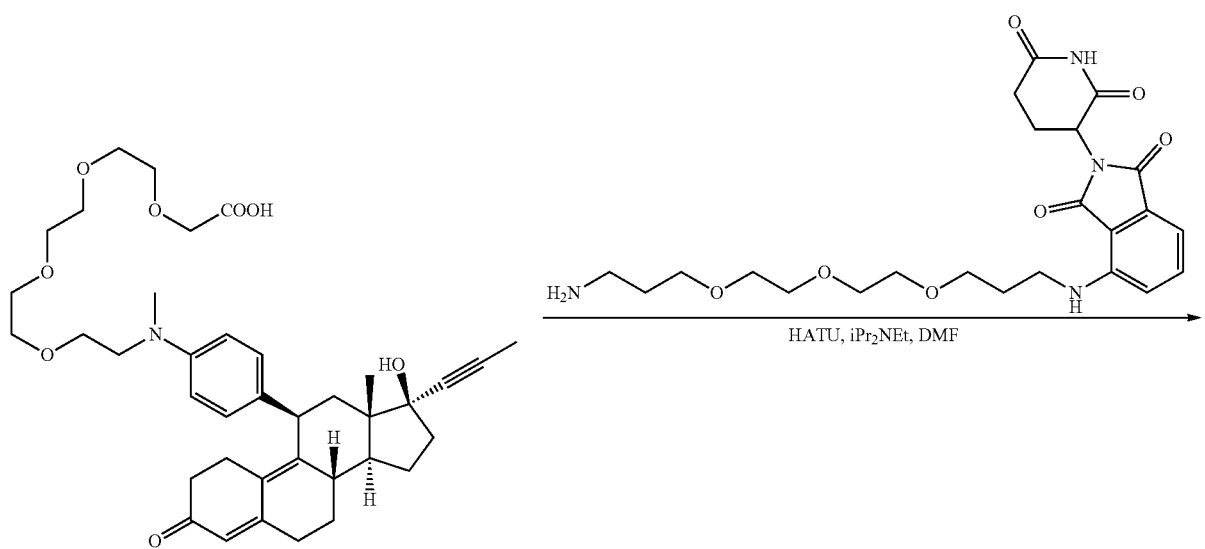

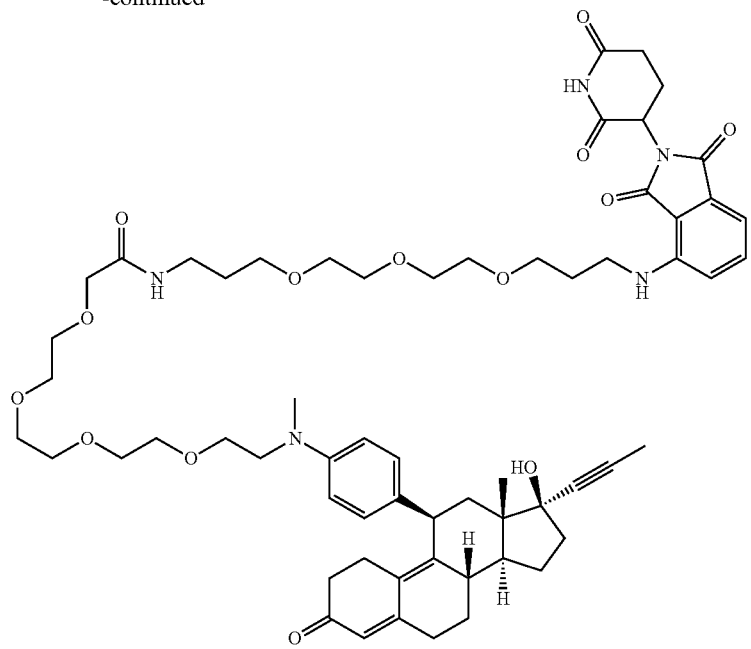

To a solution of Intermediate A (19.2 mg, 0.030 mmol) in DMSO (148 μl) were added Intermediate B (15.49 mg, 0.033 mmol), iPr$_2$NEt (10.32 μl, 0.059 mmol), and HATU (15.73 mg, 0.041 mmol) and the resulting mixture was stirred at room temperature for 12 h. The residue was purified by reverse phase preparative HPLC (Mobile phase: A=0.1% TFA/H$_2$O, B=0.1% TFA/MeCN; Gradient: B=10-90%; 20 min) to give the title compound (15.3 mg, 0.014 mmol, 46.7% yield) as a yellow amorphous material.

$^1$H-NMR (600 MHz, CDCl$_3$) δ 8.78 (s, 1H), 6.91-7.50 (m, 9H), 5.82 (s, 1H), 4.91 (m, 1H), 4.44 (m, 1H), 1.31-4.05 (m, 65H), 0.89 (s, 3H).

Example 3

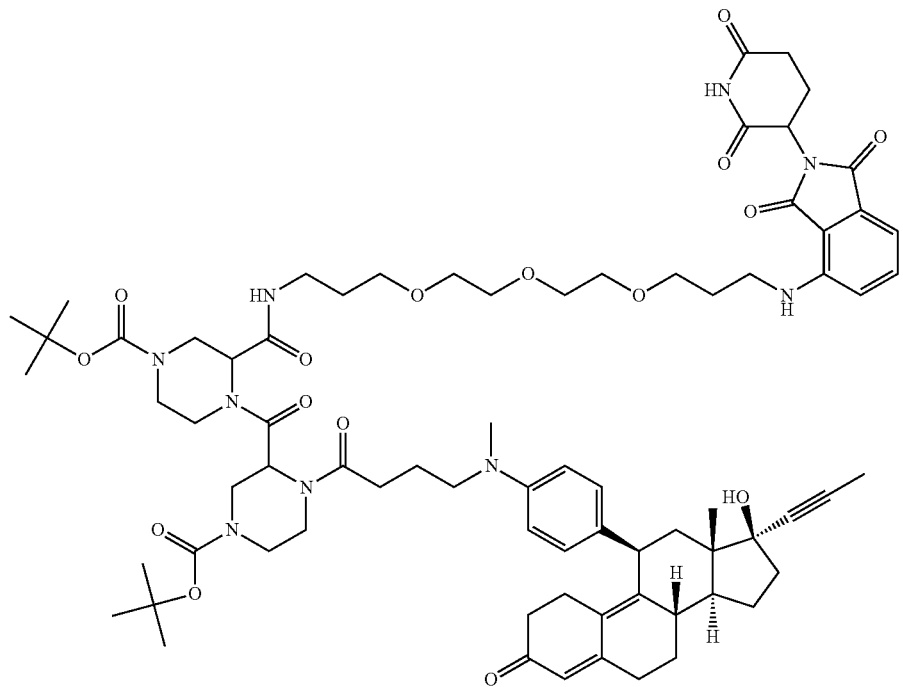

tert-Butyl-4-(4-(tert-butoxycarbonyl)-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)-3-((3-(2-(2-(3-((2-(2,6-dioxopiperidin-3-yl)-1,3-dioxoisoindolin-4-yl)amino)-propoxy)ethoxy)ethoxy)propyl)carbamoyl)piperazine-1-carboxylate

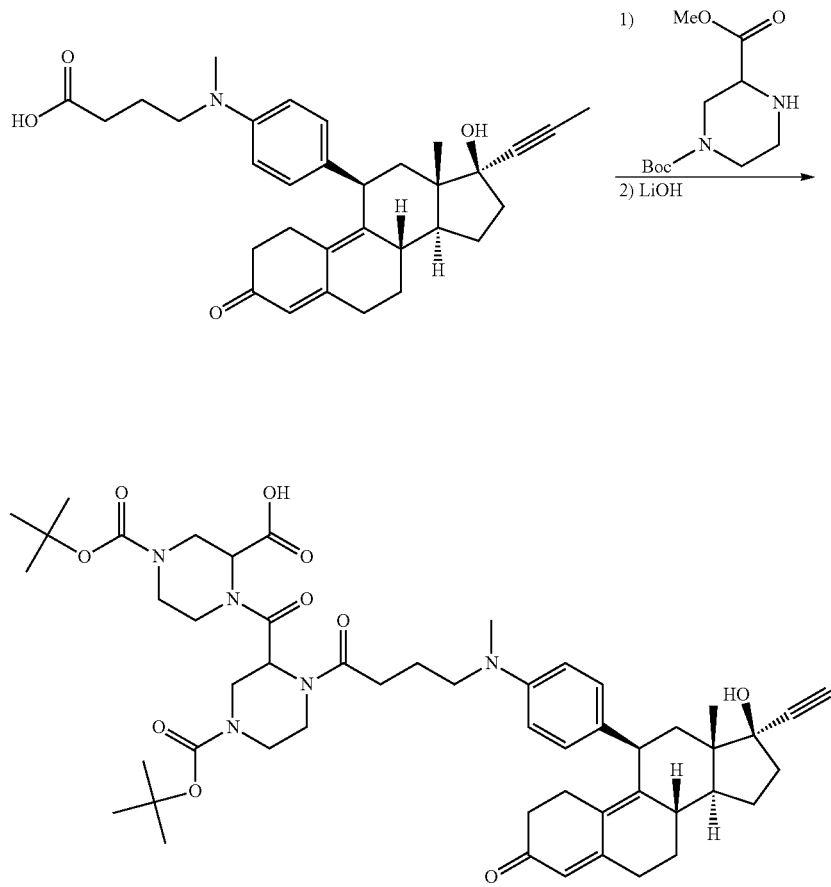

4-(tert-Butoxycarbonyl)-1-(4-(tert-butoxycarbonyl)-1-(4-((4-((8S,11R,13S,-14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)piperazine-2-carboxylic acid To a solution of Intermediate C (132 mg, 0.263 mmol) and 1-(tert-butyl) 3-methyl piperazine-1,3-dicarboxylate in DMF (1 ml) were added iPr$_2$NEt (0.092 ml, 0.526 mmol) and HATU (110 mg, 0.289 mmol) and the resulting mixture was stirred at room temperature for 12 h. The reaction mixture was diluted with EtOAc (20 mL) and washed with sat NH$_4$Cl (20 mL), water (20 mL×3), and brine (20 mL). The organic layer was dried over Na$_2$SO$_4$, filtered and concentrated under reduced pressure. The residue was dissolved in 1.0 mL of THF and 0.4 mL of water and treated with LiOH and stirred at room temperature for 1 hour. The residue was purified by reverse phase preparative HPLC (Mobile phase: A=0.1% TFA/H$_2$O, B=0.1% TFA/MeCN; Gradient: B=10-90%; 20 min) to give the title compound (13.1 mg, 0.014 mmol, 5.38% yield) as a brown amorphous material.

$^1$H-NMR (600 MHz, CDCl$_3$) δ 7.29-7.41 (m, 5H), 5.85 (s, 1H), 1.30-5.20 (m, 44H), 1.42 (two singlets, 18H), 0.49 (s, 3H).

Also obtained was 4-(tert-butoxycarbonyl)-1-(4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carboxylic acid (119.8 mg, 0.168 mmol, 63.8% yield) as a tan amorphous material.

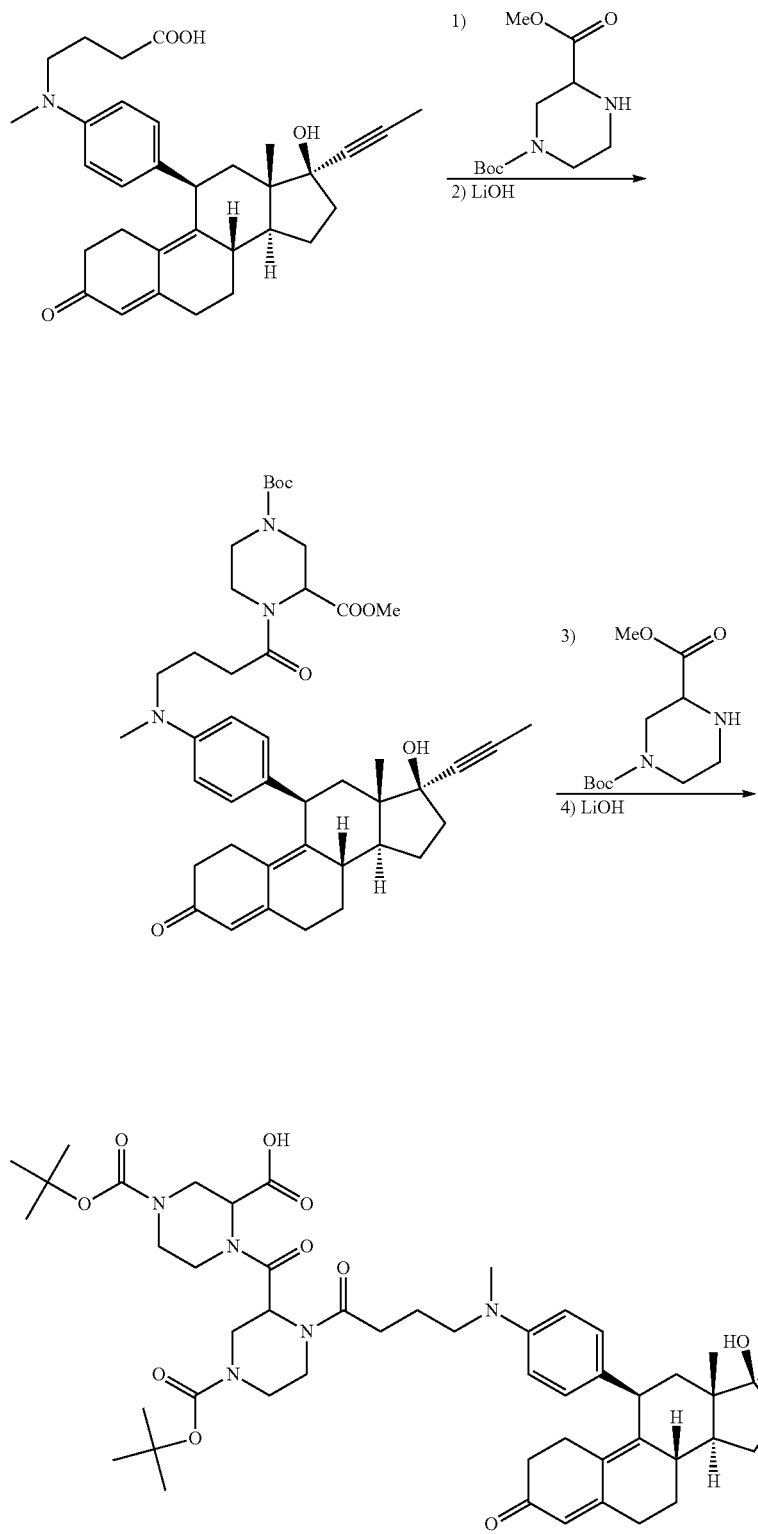

Alternatively, the title compound can be prepared via the mono-piperidine compound, shown in the above scheme, beginning with Intermediate C, using two stepwise pairs of (a) amino acid coupling from with 1-(tert-butyl) 3-methyl piperazine-1,3-dicarboxylate, and (b) ester hydrolysis. HATU and DIPEA in DMF were employed at room temperature for 12 hours for the coupling reactions. The hydrolyses were accomplished with LiOH at room temperature for one hour. The combination of coupling and hydrolysis occurred in roughly 60% yield when performed on a gram scale. The steps could be accomplished by someone skilled in the art.

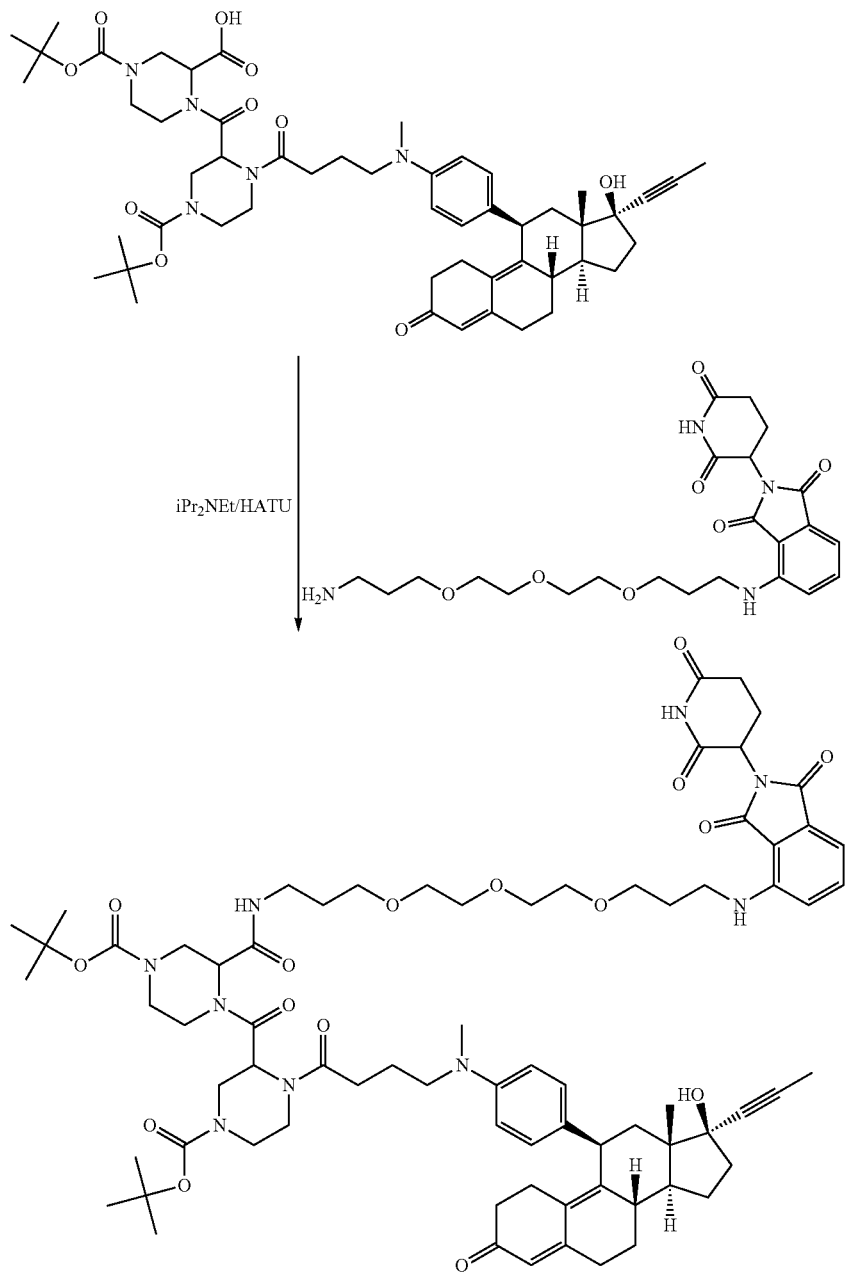

tert-Butyl-4-(4-(tert-butoxycarbonyl)-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)-3-((3-(2-(2-(3-((2-(2,6-dioxopiperidin-3-yl)-1,3-dioxoisoindolin-4-yl)amino)propoxy)ethoxy)-ethoxy)propyl)carbamoyl)piperazine-1-carboxylate To a solution of Intermediate B (8.43 mg, 0.018 mmol) and the product from the previous step (13.1 mg, 0.014 mmol) in DMF (0.1 ml) were added iPr₂NEt (6.18 µl, 0.035 mmol) and HATU (7.53 mg, 0.020 mmol) and the resulting mixture was stirred at room temperature for 12 h. The residue was purified by reverse phase preparative HPLC (Mobile phase: A=0.1% TFA/H₂O, B=0.1% TFA/MeCN; Gradient: B=10-90%; 20 min) to give the title compound as a yellow amorphous material. The compound was greater than 95% pure by reverse phase HPLC-MS with UV/vis and MS detection (M+H=1385).

$^1$H-NMR (600 MHz, CDCl$_3$) δ 8.81 (s, 1H), 8.62 (s, 1H), 7.41 (d, J=7.5 Hz, 1H), 6.99 (m, 5H), 6.61 (m, 3H), 5.78 (s, 1H), 4.80 (m, 3H), 4.20 (s, 2H), 3.00-4.00 (m, 31H), 1.65-3.00 (m, 31H), 1.42 (m, 18H), 1.34 (m, 3H), 0.62 (s, 3H).

$^{13}$C-NMR (600 MHz, CDCl$_3$) δ 199.6, 173.8, 171.3, 171.2, 169.3, 168.5, 167.7, 157.0, 155.1, 147.4, 147.0, 146.9, 136.1, 132.5, 131.8, 129.0, 127.6, 122.7, 116.7, 112.4, 111.3, 109.9, 82.4, 80.3, 80.1, 80.0, 70.5, 70.4, 70.1, 69.2, 69.0, 68.0, 54.9, 53.6, 53.3, 50.5, 48.0, 46.9, 46.1, 42.5, 41.7, 40.9, 39.5, 38.8, 38.1, 37.1, 36.9, 31.5, 31.1, 29.7, 29.3, 28.2, 27.3, 25.8, 23.3, 22.8, 22.3, 22.0, 13.8, 3.8.

Example 4

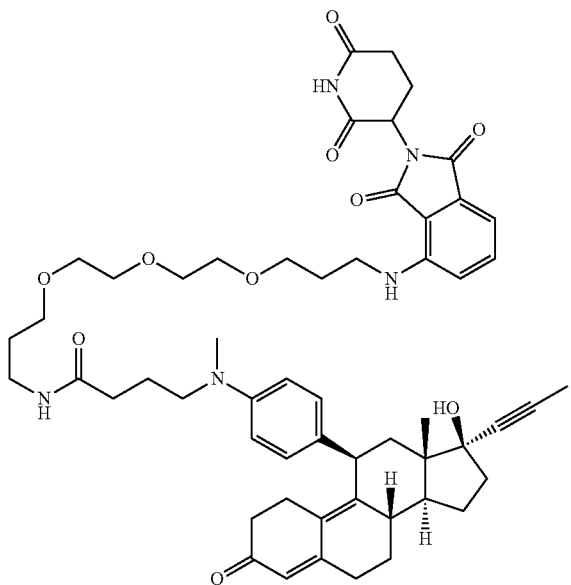

N-(3-(2-(2-(3-((2-(2,6-Dioxopiperidin-3-yl)-1,3-dioxoisoindolin-4-yl)amino)propoxy)-ethoxy)ethoxy)propyl)-4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanamide To a solution of Intermediate C (15.1 mg, 0.030 mmol) were added Intermediate B (17.93 mg, 0.038 mmol) in DMSO and iPr$_2$NEt (7.89 μl, 0.045 mmol) plus HATU (17.17 mg, 0.045 mmol) was then added. The resulting mixture was stirred at room temperature for 12 h. The residue was purified by reverse phase preparative HPLC (Mobile phase: A=0.1% TFA/H2O, B=0.1% TFA/MeCN; Gradient: B=0-70%; 12 min) to give the title compound (19.3 mg, 0.020 mmol, 66.8% yield) as a yellow amorphous material. The compound was greater than 95% pure by reverse phase HPLC-MS with UV/vis and MS detection (M+H=960).

$^1$H-NMR (600 MHz, CDCl$_3$) δ 8.55 (s, 1H), 6.88-7.40 (m, 9H), 5.82 (s, 1H), 4.91 (s, 1H), 4.44 (s, 1H), 3.18-3.78 (m, 19H), 1.40-2.98 (m, 35H), 0.49 (s, 3H).

$^{13}$C-NMR (600 MHz, CDCl$_3$) δ 199.8, 173.5, 171.4, 169.4, 168.8, 167.7, 157.0, 147.7, 147.0, 144.6, 138.3, 136.9, 132.8, 130.1, 129.3, 123.0, 116.8, 111.4, 109.8, 79.7, 79.3, 76.8, 70.3, 69.9, 69.7, 59.6, 49.6, 48.9, 46.9, 45.8, 40.5, 40.2, 39.2, 39.1, 38.9, 38.5, 36.5, 33.4, 31.4, 31.1, 29.05, 28.3, 27.3, 25.8, 23.3, 22.8, 20.7, 14.0, 3.8.

The following compounds were prepared using methods similar to those disclosed above.

| EX | Structure | Name |
|---|---|---|
| 5 | 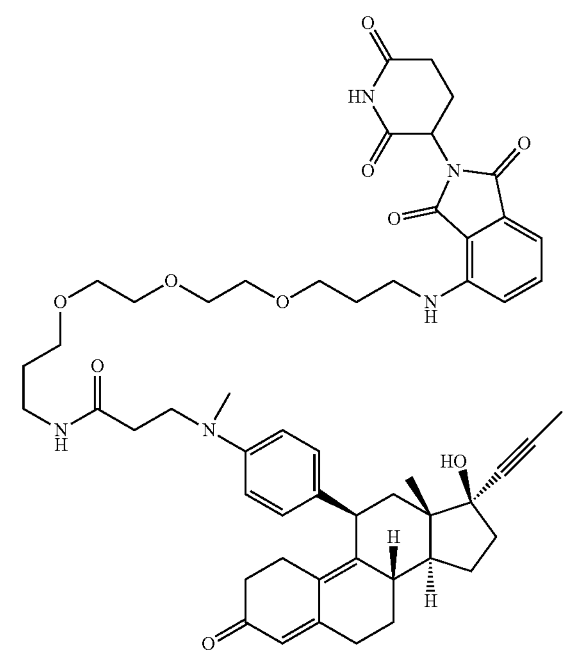 | N-(3-(2-(2-(3-((2-(2,6-dioxopiperidin-3-yl)-1,3-dioxoisoindolin-4-yl)amino)-propoxy)ethoxy)ethoxy)propyl)-3-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)-amino)propanamide |

| EX | Structure | Name |
|---|---|---|
| 6 | 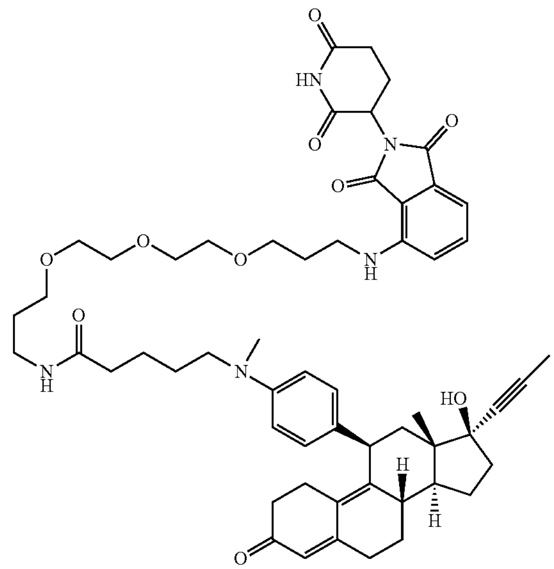 | N-(3-(2-(2-(3-((2-(2,6-dioxopiperidin-3-yl)-1,3-dioxoisoindolin-4-yl)-amino)propoxy)ethoxy)ethoxy)propyl)-5-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)-amino)pentanamide |
| 7 | 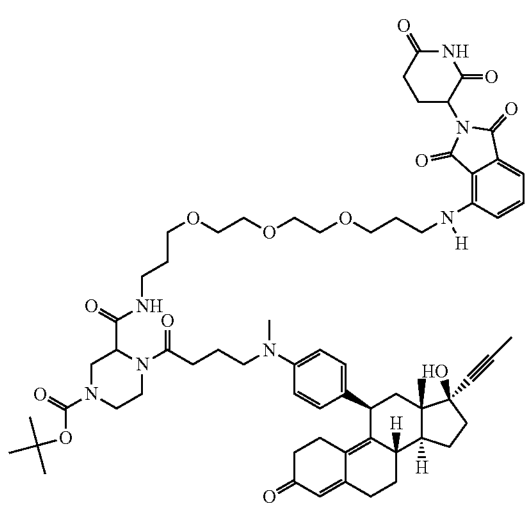 | tert-Butyl 3-((3-(2-(2-(3-((2-(2,6-dioxopiperidin-3-yl)-1,3-dioxoisoindolin-4-yl)-amino)propoxy)ethoxy)-ethoxy)propyl)carbamoyl)-4-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)-amino)butanoyl)piperazine-1-carboxylate |

The following compounds can generally be made using the methods described above. It is expected that these compounds when made will have activity similar to those that have been made in the examples above.

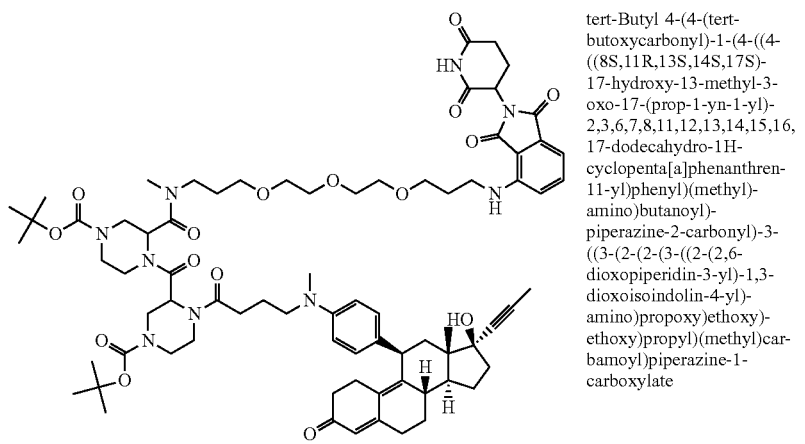

tert-Butyl 4-(4-(tert-butoxycarbonyl)-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)-amino)butanoyl)-piperazine-2-carbonyl)-3-((3-(2-(2-(3-((2-(2,6-dioxopiperidin-3-yl)-1,3-dioxoisoindolin-4-yl)-amino)propoxy)ethoxy)-ethoxy)propyl)(methyl)carbamoyl)piperazine-1-carboxylate

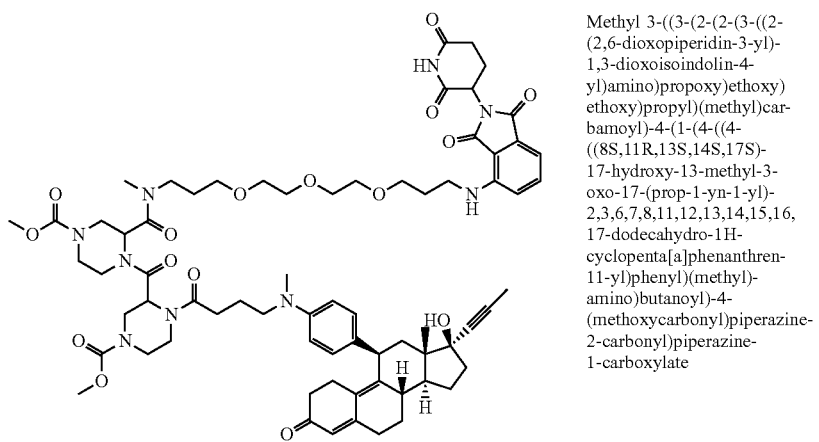

Methyl 3-((3-(2-(2-(3-((2-(2,6-dioxopiperidin-3-yl)-1,3-dioxoisoindolin-4-yl)amino)propoxy)ethoxy)ethoxy)propyl)(methyl)carbamoyl)-4-(1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)-amino)butanoyl)-4-(methoxycarbonyl)piperazine-2-carbonyl)piperazine-1-carboxylate

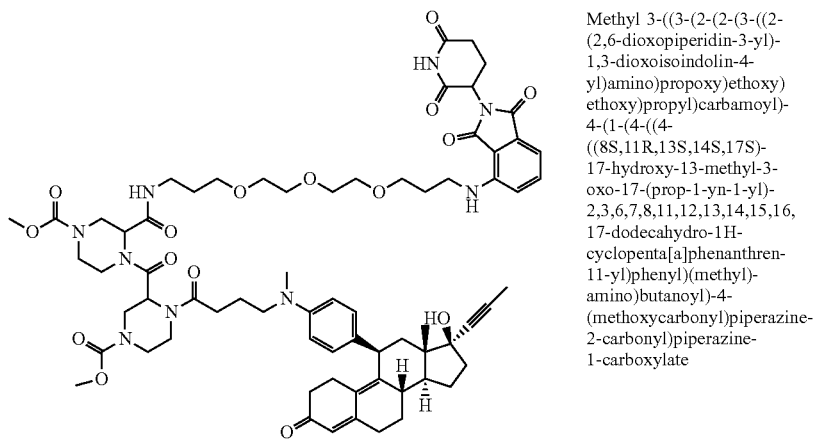

Methyl 3-((3-(2-(2-(3-((2-(2,6-dioxopiperidin-3-yl)-1,3-dioxoisoindolin-4-yl)amino)propoxy)ethoxy)ethoxy)propyl)carbamoyl)-4-(1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)-amino)butanoyl)-4-(methoxycarbonyl)piperazine-2-carbonyl)piperazine-1-carboxylate

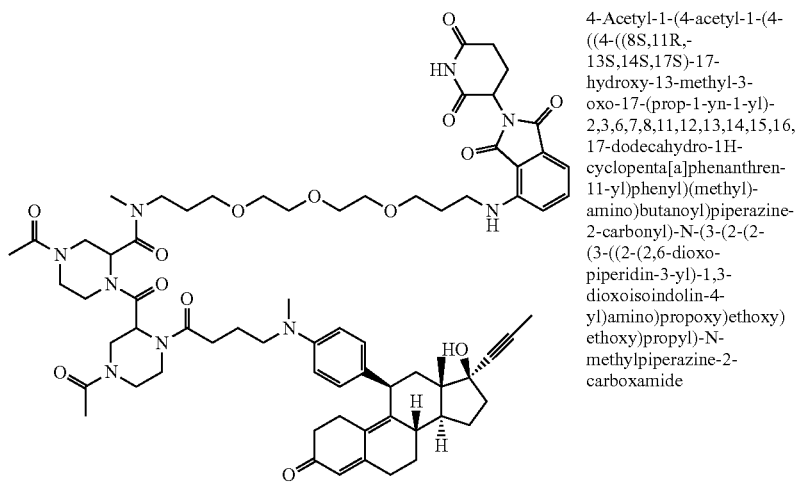

4-Acetyl-1-(4-acetyl-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)-N-(3-(2-(2-(3-((2-(2,6-dioxopiperidin-3-yl)-1,3-dioxoisoindolin-4-yl)amino)propoxy)ethoxy)ethoxy)propyl)-N-methylpiperazine-2-carboxamide

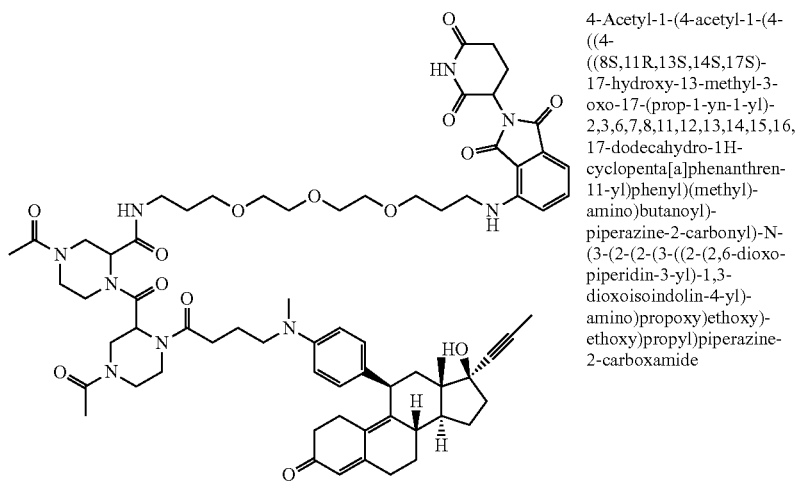

4-Acetyl-1-(4-acetyl-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)-N-(3-(2-(2-(3-((2-(2,6-dioxopiperidin-3-yl)-1,3-dioxoisoindolin-4-yl)amino)propoxy)ethoxy)ethoxy)propyl)piperazine-2-carboxamide

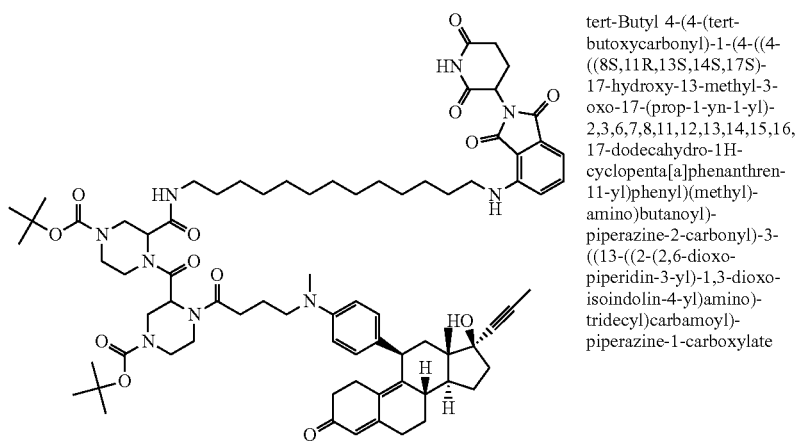

tert-Butyl 4-(4-(tert-butoxycarbonyl)-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)-3-((13-((2-(2,6-dioxopiperidin-3-yl)-1,3-dioxoisoindolin-4-yl)amino)tridecyl)carbamoyl)piperazine-1-carboxylate

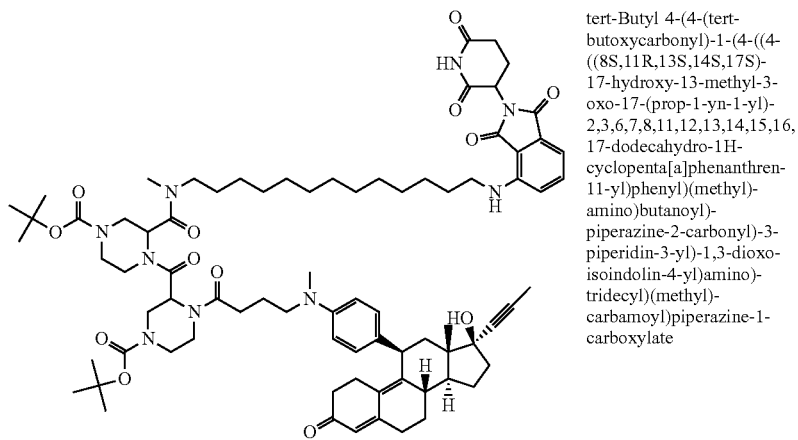

tert-Butyl 4-(4-(tert-butoxycarbonyl)-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)-3-piperidin-3-yl)-1,3-dioxoisoindolin-4-yl)amino)tridecyl)(methyl)carbamoyl)piperazine-1-carboxylate

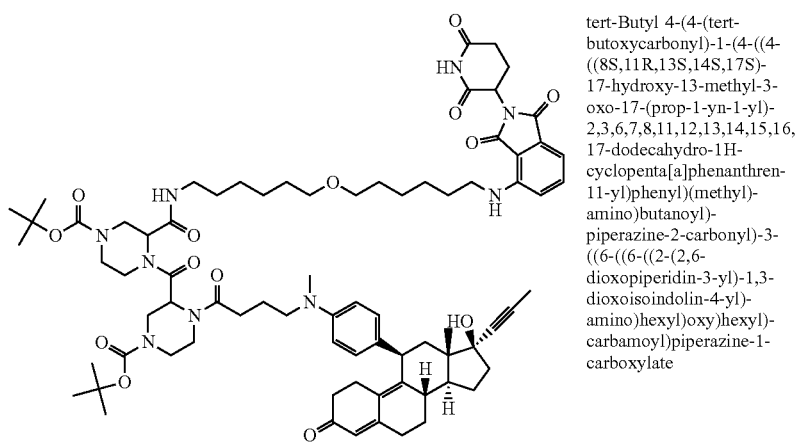

tert-Butyl 4-(4-(tert-butoxycarbonyl)-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)-3-((6-((6-((2-(2,6-dioxopiperidin-3-yl)-1,3-dioxoisoindolin-4-yl)amino)hexyl)oxy)hexyl)carbamoyl)piperazine-1-carboxylate

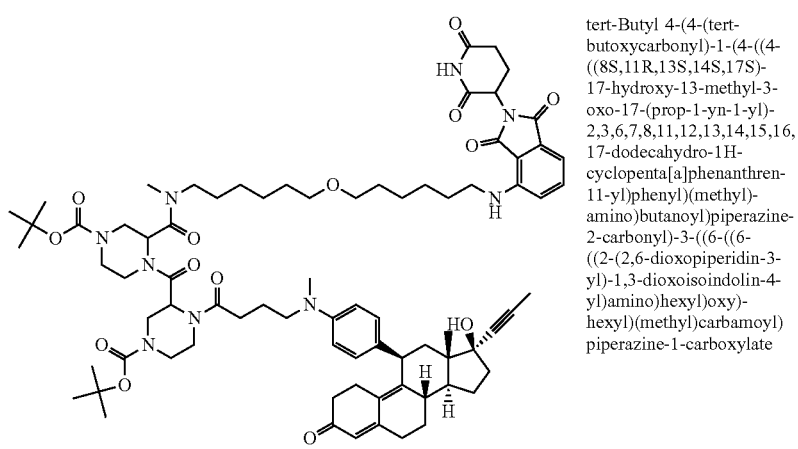

tert-Butyl 4-(4-(tert-butoxycarbonyl)-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)amino)butanoyl)piperazine-2-carbonyl)-3-((6-((6-((2-(2,6-dioxopiperidin-3-yl)-1,3-dioxoisoindolin-4-yl)amino)hexyl)oxy)hexyl)(methyl)carbamoyl)piperazine-1-carboxylate

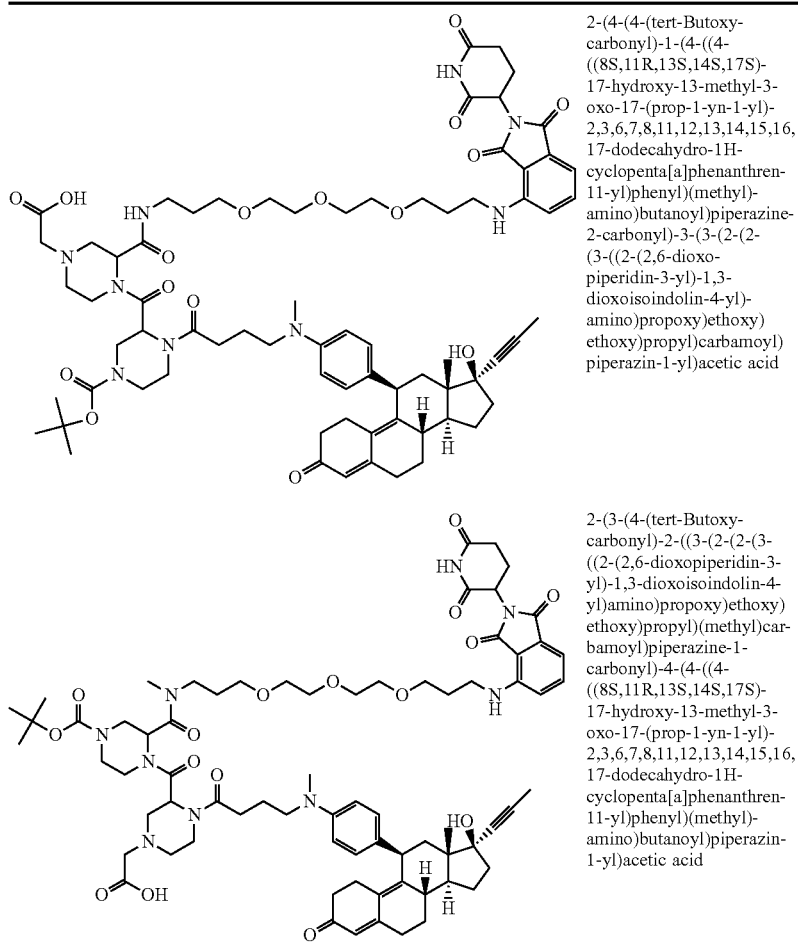

2-(4-(4-(tert-Butoxy-carbonyl)-1-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)-amino)butanoyl)piperazine-2-carbonyl)-3-(3-(2-(2-(3-((2-(2,6-dioxo-piperidin-3-yl)-1,3-dioxoisoindolin-4-yl)-amino)propoxy)ethoxy)ethoxy)propyl)carbamoyl)piperazin-1-yl)acetic acid 2-(3-(4-(tert-Butoxy-carbonyl)-2-((3-(2-(2-(3-((2-(2,6-dioxopiperidin-3-yl)-1,3-dioxoisoindolin-4-yl)amino)propoxy)ethoxy)ethoxy)propyl)(methyl)carbamoyl)piperazine-1-carbonyl)-4-(4-((4-((8S,11R,13S,14S,17S)-17-hydroxy-13-methyl-3-oxo-17-(prop-1-yn-1-yl)-2,3,6,7,8,11,12,13,14,15,16,17-dodecahydro-1H-cyclopenta[a]phenanthren-11-yl)phenyl)(methyl)-amino)butanoyl)piperazin-1-yl)acetic acid The activity of the compounds in Examples 1-4 as glucocorticoid receptor modulators is illustrated in the following assays. The other compounds listed above, which have not yet been made and/or tested, are predicted to have activity in these assays as well.

Biological Activity Assay

Single Dose Subcutaneous Pharmacokinetics in CD-1 Mice

The intraperitoneal bioavailability was determined in the following study: three CD-1 female mice were dosed by intraperitoneal injection (10 mg/kg) and plasma collected at the following hourly time points (0.083, 0.25, 0.5, 1, 2, 48 and 24h). Plasma concentration was determined by HPLC-MS. Results of dosage with Example 3 are shown in Table 1.

Glucocorticoid Receptor (GR) Degradation Assay in H1299 Cells

Compounds of the present disclosure are assessed for their activity in degrading GR in A549 and H1299 cells using the western blot method. The assay is carried out in the presence of 10% fetal bovine serum (FBS) or high percentage of human or mouse serum. Protocols of the western blot assay are described below.

1. Cells are split with 0.5% Trypsin, 5 min 37° C.
2. Carry ¼ & ¼ in growth media: RPMI with 10% FBS
3. In each cell of a 6 well plate are combined 300,000 cells and 2 mL growth media.
4. Culture is allowed to grow for 24 hours
5. Media are gently removed and replaced with 2 mL fresh growth media
6. Compounds are diluted in DMSO, beginning with 10 mM, and continuing with serial dilutions into 1 mM, 100 μM, 10 μM and 1 μM.
7. Samples are transferred in 2 μL portions into media using Eppendorf pipets. Media is gently swirled to mix. Samples are incubated at 37° C., 5% $CO_2$ for 8 hours.
8. Media are aspirated and washed with 2 mL PBS.
9. To the plates are added 200 μL of ice cold cell lysis buffer.
10. Samples are set on ice for 15 min, then scraped using Cell Lifter into 1.5 mL Eppendorf tubes.
11. Samples are centrifuged at 15000 rpm. Supernatant, representing the soluble fraction, is removed.
12. 60 μL is transferred into Eppendorf tubes. To each sample is added 20 μL of 4× gel loading solution.
13. Samples are heated to 95° C. for 10 minutes, then centrifuged for 1 minute at 15000 rpm.
14. Pre-cast gels (BioRad) in tris-glycin-SDS running buffer are prepared.
15. 10 μL of prepared lysate, from step 12, is loaded.
16. Gels are run until the dye front reaches the end of gel. Samples are transferred onto nitrocellulose membranes using semi-dry method using transfer machine (BioRad) into preassembled transfer packs (BioRad) for 10 minutes.

17. Nitrocellulose membranes are rinsed with TBST and cut into a top part, for GR, and a bottom part, for actin.
18. Samples are blocked in 5% milk in TBST for 1 hour.
19. GR antibody (Cell Signaling technology, 1/1000 diluted in 5% BSA in TBST) is added to the upper membrane, and actin antibody (1/5000) is added to the lower membrane. Samples are stored overnight at 4° C.
20. Samples are washed with 4×TBST for 10 min
21. Anti-mouse and anti-rabbit are prepared with HRP 2° 1/5000 5% milk in TBST 30 min to 1 hour at rt.
22. Samples are washed with 5×TBST, 10 min for each wash.
23. Samples are developed using pico ECL reagent.
24. Membranes are exposed to X-ray films for 5-20 sec in the dark room.
25. Membranes are developed using the x-ray film developer.

PC3 Cell Line Clonogenic (Colony Formation) Assay

PC3 cells are routinely maintained in RPMI 1640 media. Cell growth is determined using crystal violet staining. Cells are initially seeded at density of 1000 to 2000 cells per well in 6-well plates. 24 hours post-seeding, cells are treated with DMSO control, enzalutamide, RU-486 or various GR degraders at 3.3 µM or 10 µM concentration. Cells are allowed to grow under regular growth conditions for 10-14 days. Cells are then fixed with 80% MeOH and stained with crystal violet solution (0.05%) overnight. Plates are then washed in water, dried and scanned. Results are presented in FIG. 2. Example 3, disclosed herein, inhibited colony formation, whereas RU-486 and enzalutamide did not differ significantly from control.

DU145 Cell Line Proliferation Assay

DU145 cells are routinely maintained in RPMI 1640 media. Proliferation is determined using a real time cell imaging device, Incucyte. Cells are initially seeded at density of 2000 cells per well in 96-well plates. 24 hours post-seeding, cells are treated with DMSO control or GR degraders at 1 µM, 3.3 µM or 10 µM concentration. Cells are allowed to grow under regular growth conditions for 5 days while being monitored and imaged every four hours by Incucyte. Confluency of cells, a surrogate for proliferation, is calculated and plotted. Results are presented in FIG. 3. Example 3, disclosed herein, displays efficacy against DU145 cancer cells; similar assay with enzalutamide did not differ significantly from control (data not shown).

Immunohistochemistry to Visualize GR Degradation In Vivo

NCR-Nude mice are injected with vehicle or different doses of GR degrader (5, 20, and 66 mg/kg) once intraperitoneally. Liver tissue are fixed in formalin for 24 hours, paraffin embedded, sectioned and stained according to standard procedures. Endogenous peroxidases are briefly inactivated by 3% hydrogen peroxide. Non-specific signals are blocked using 3% BSA, 10% goat serum in 0.1% Triton X-100. After antigen retrieval in citrate buffer, slides are stained using respective antibodies overnight at 4° C., GR (Cell Signaling D8H2 #3660, 1:4000). After overnight incubation, the slides are washed and incubated with secondary antibody (HRP-polymers, Biocare Medical) for 30 min at room temperature. The slides are washed three times and stained with DAB substrate (ThermoFisher Scientific). The slides are then counterstained with hematoxylin and mounted with mounting medium. Results are shown in FIG. 4. The staining reveals strong nuclear presence of GR in the liver of control treated mice whereas GR degrader treated mice have livers with absent or greatly diminished presence of GR protein.

Immunohistochemistry to Visualize GR Degradation In Vivo

Figure 5:
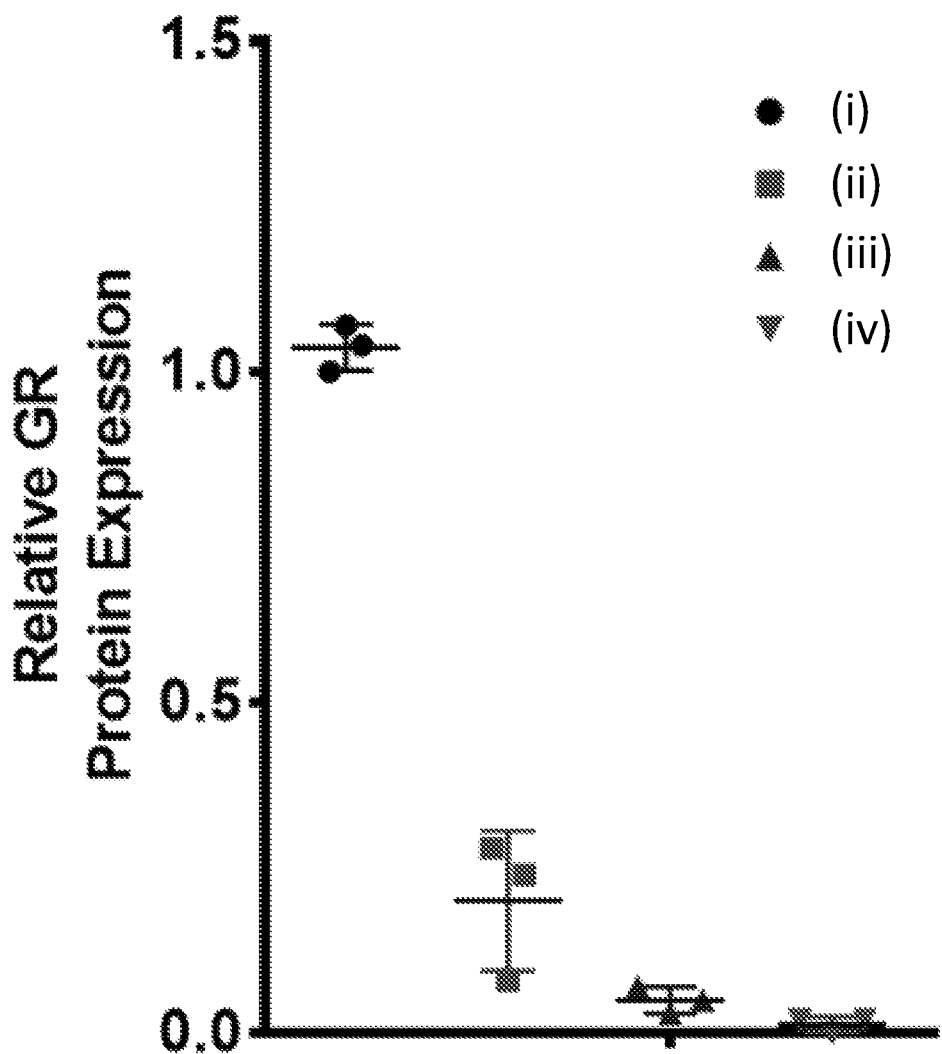
FIG. 5 illustrates quantification of GR protein levels in the liver of mice treated once intraperitoneally with (i, circles) vehicle, or Example 3 at: (ii, squares) 5 mg/kg, (iii, triangles) 20 mg/kg or (iv, inverted triangles) 66.6 mg/kg concentration. Tissue harvested 24 hours after a single dose.

NCR-Nude mice were injected with vehicle or different doses of GR degrader (5, 20 and 66 mg/kg) once intraperitoneally. Liver tissue were fixed in formalin for 24 hours, paraffin embedded, sectioned and stained according to standard procedures. Briefly, endogenous peroxidases were inactivated by 3% hydrogen peroxide. Non-specific signals were blocked using 3% BSA, 10% goat serum in 0.1% Triton X-100. After antigen retrieval in citrate buffer, slides were stained using respective antibodies overnight at 4° C., GR (Cell Signaling D8H2 #3660, 1:4000). After overnight incubation, the slides were washed and incubated with secondary antibody (HRP-polymers, Biocare Medical) for 30 min at room temperature. The slides were washed three times and stained with DAB substrate (ThermoFisher Scientific). The slides were then counterstained with hematoxylin and mounted with mounting medium. FIG. 5 illustrates quantification of GR protein levels in the liver of mice treated once intraperitoneally with (i, circles) vehicle, or Example 3 at: (ii, squares) 5 mg/kg, (iii, triangles) 20 mg/kg or (iv, inverted triangles) 66.6 mg/kg concentration.

Quantification of GR Degradation In Vivo

NCR-Nude mice are injected with vehicle or different doses of GR degrader (5, 20 and 66 mg/kg) once intraperitoneally. Liver tissue is harvested and snap frozen in liquid $N_2$. A 5 mm size fragment is then chopped off, and lysed in RIPA lysis buffer with the aid of a bullet blender. Lysates are centrifuged at 15000 rpm for 15 minutes. Supernatant is taken and protein quantification is performed using the BioRad DC method. A total of 10 µg protein is loaded on pre-cast gels and western blots are performed as described in detail above.

Table 1 illustrates pharmacokinetic properties of the Example 3 compound in CD-1 mice (n=3) after a single intraperitoneal dose of 10 mg/kg. From these data the following PK properties are obtained: $T_{max}$=4.00 hr; $C_{max}$=3.24 µM; regression time=N/A; terminal $T_{max}$=N/A; $AUC_{last}$=46.2 hr*µM; $AUC_{inf}$=N/A.

TABLE 1

Pharmacokinetic properties.

| Sampling time, hr | Individual concentration (µM) | | | Mean (µM) | SD | CV (%) |
|---|---|---|---|---|---|---|
| pre-dose | BQL | BQL | BQL | BQL | N/A | N/A |
| 0.083 | 0.114 | 0.0722 | 0.135 | 0.107 | 0.0320 | 29.9 |
| 0.25 | 0.283 | 0.0930 | 0.173 | 0.183 | 0.0954 | 52.1 |
| 0.5 | 0.727 | 0.652 | 0.939 | 0.773 | 0.149 | 19.2 |
| 1 | 1.01 | 0.147 | 0.358 | 0.505 | 0.451 | 89.2 |
| 2 | 2.24 | 1.48 | 2.87 | 2.20 | 0.696 | 31.7 |
| 4 | 3.30 | 3.22 | 3.21 | 3.24 | 0.0514 | 1.59 |
| 8 | 2.90 | 2.98 | 2.61 | 2.83 | 0.198 | 6.99 |
| 24 | 0.440 | 0.505 | 0.617 | 0.521 | 0.0893 | 17.2 |

Figure 6:
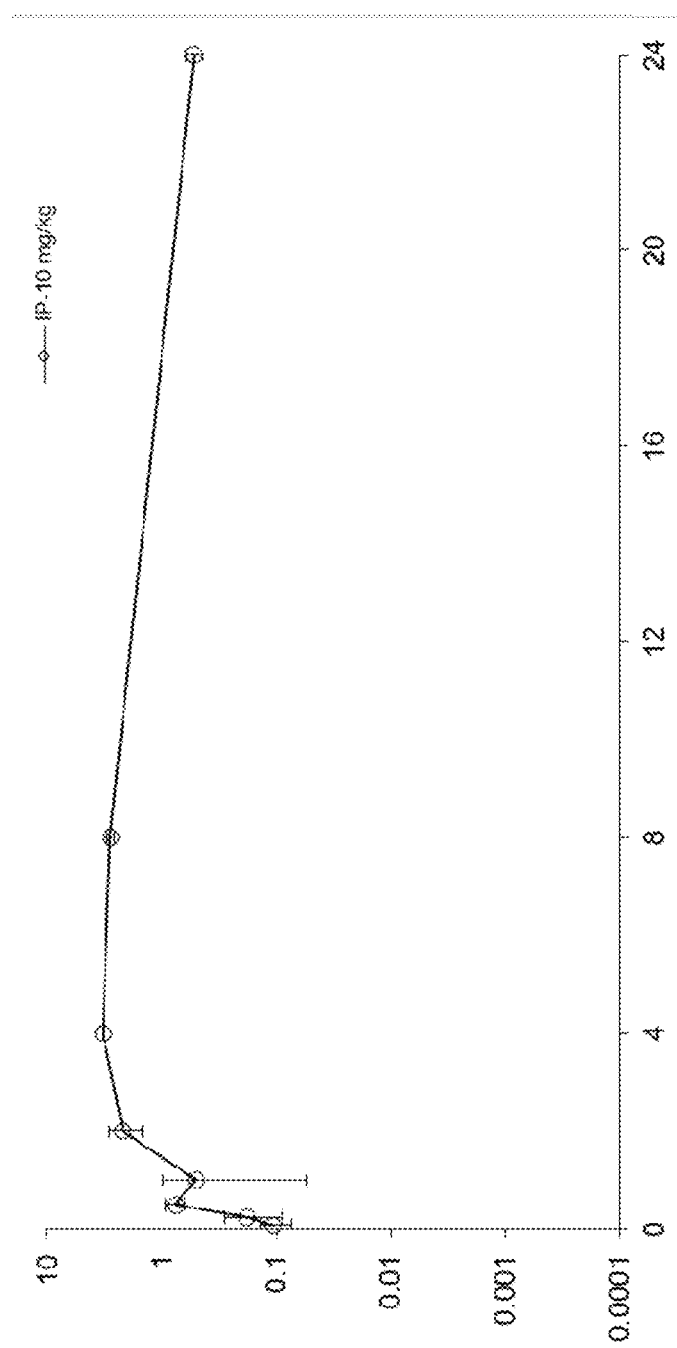
FIG. 6 illustrates mean plasma concentration/time profiles of Example 3 after intraperitoneal dose in female CD1 mice (N=3/timepoint).

Data are also shown in FIG. 6, illustrating the mean plasma concentration/time profiles of Example 3 after intraperitoneal dose in female CD1 mice (N=3/timepoint).

In Vivo Anti-Tumor Efficacy Study in Male CB17 SCID Mice Using VCaP Castration Resistant Prostate Cancer (CRPC) Xenograft Model $1×10^7$ VCaP cells were injected into the flanks of male CB17 SCID Mice. Tumor take was monitored visually and by palpation bi-weekly. Once tumors reached 200 $mm^3$ mice were castrated. Once tumors stopped shrinking, mice were randomized into control and different treatment groups for 26 days. Treatment cohorts are as follows:

a. Vehicle is 5% Cremophor: 5% Ethanol in saline, (n=10 animals)
b. GR degrader example #3 (100 mg/kg) IP once daily in 5% Cremophor: 5% Ethanol in saline (n=10 animals)
c. Enzalutamide (10 mg/kg) IP once daily in 5% Cremophor: 5% Ethanol in saline (n=10 animals)
d. GR degrader example #3 (100 mg/kg)+Enzalutamide (10 mg/kg) IP once daily in 5% Cremophor: 5% Ethanol in saline (n=10 animals)

Figure 7:
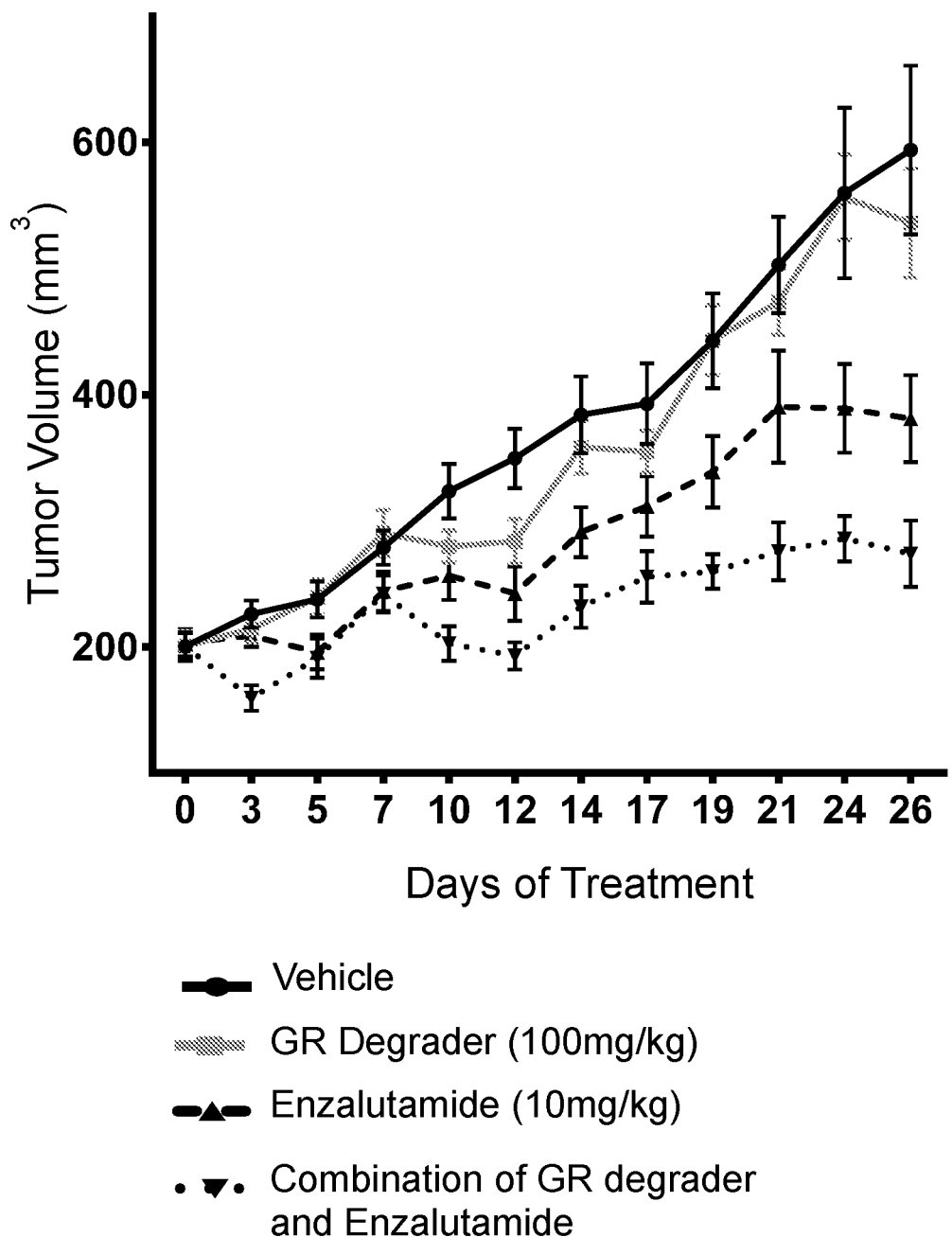
FIG. 7 illustrates xenograft tumor growth measurements of Male CB17 SCID Mice implanted with VCaP prostate cancer cells, castrated and treated with vehicle control, enzalutamide (10 mg/kg) alone, GR degrader Example #3 (100 mg/kg) alone or combination of enzalutamide (10 mg/kg) and GR degrader Example #3 (100 mg/kg) for 28 days. The data shows that GR degraders synergize with enzalutamide to inhibit growth of prostate cancer.

Tumor diameter and volume were calculated based on caliper measurements of tumor length and height using the formula tumor volume=(length×width$^2$)/2. Tumor volume and body weight were measured three times a week. As shown in in FIG. 7, the GR degrader Example 3 synergizes with enzalutamide to inhibit growth of prostate cancer; similar synergy is expected when other GR degraders are used in combination with enzalutamide or another antiandrogen.

In Vivo Anti-Tumor Efficacy Study in Immunocompetent Male C57/Bl6 Mice

TRAMP-C1 cells (5×10$^6$) were injected into the flanks of male C57/Bl6 mice. Tumor take was monitored visually and by palpation bi-weekly. Once tumors reached 200 mm$^3$ mice were randomized into control and different treatment groups for 7 days. Treatment cohorts are as follows:
a. Vehicle is 5% Cremophor: 5% Ethanol in saline, (n=10 animals)
b. GR degrader Example #3 (100 mg/kg) IP once daily in 5% Cremophor: 5% Ethanol in saline (n=10 animals)
c. Anti-PD1 antibody, clone RMP1-14 (200 μg) IP once daily in 5% Cremophor: 5% Ethanol in saline (n=10 animals)
d. GR degrader Example #3 (100 mg/kg)+Anti-PD1 antibody (200 μg) IP once daily in 5% Cremophor: 5% Ethanol in saline (n=10 animals)

Figure 8:
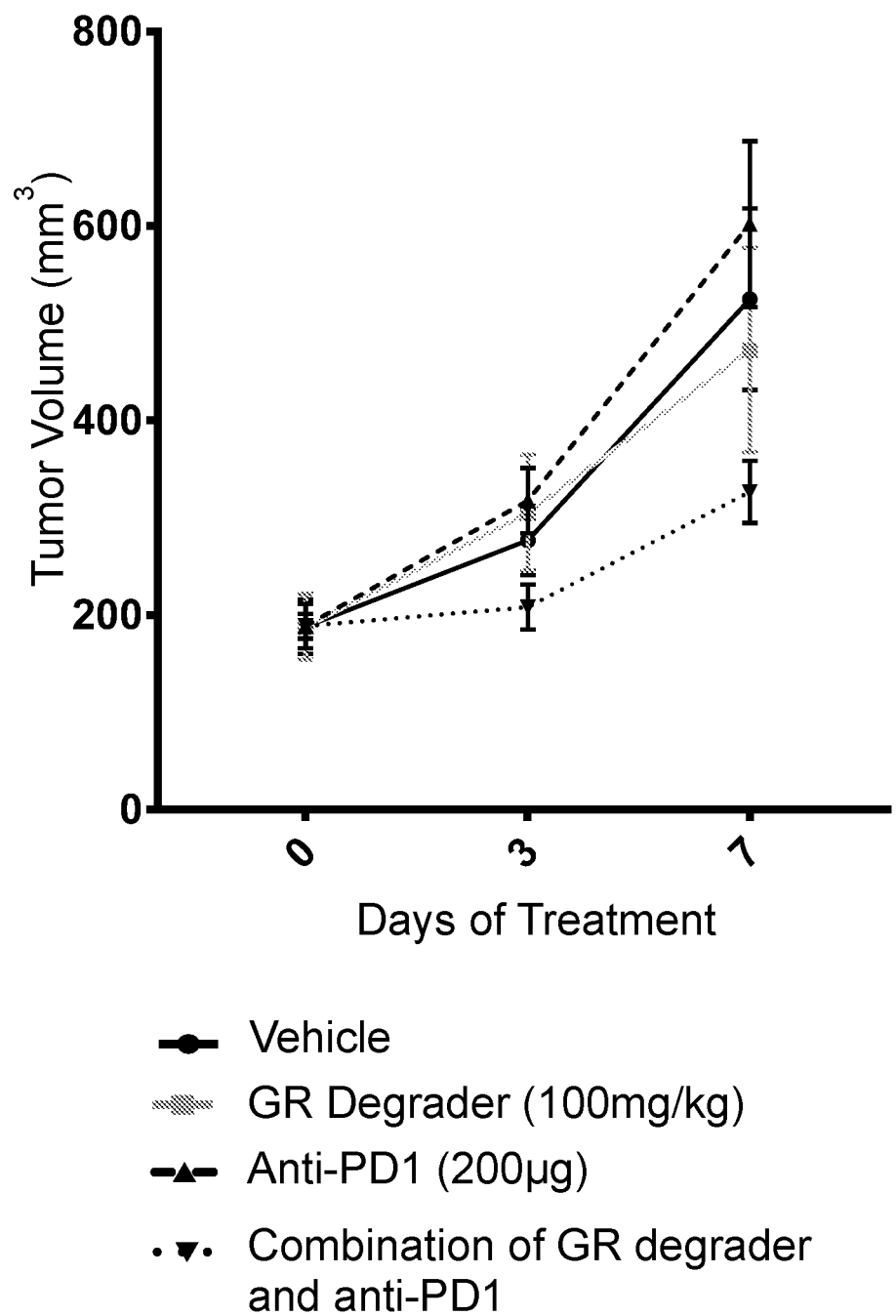
FIG. 8 illustrates tumor growth measurements of C57/Bl6 immunocompetent mice implanted with TRAMP-C1 prostate cancer cells, and treated with vehicle control, anti-PD1 antibody (200 μg) alone, GR degrader Example #3 (100 mg/kg) alone or combination of anti-PD1 antibody (200 μg) and GR degrader Example #3 (100 mg/kg) for 7 days. The data shows that GR degraders synergize with anti-PD1 antibody to inhibit growth of prostate cancer.

Tumor diameter and volume were calculated based on caliper measurements of tumor length and height using the formula tumor volume=(length×width$^2$)/2. Tumor volume and body weight were measured three times. As shown in in FIG. 8, the GR degrader Example 3 synergizes with anti-PD1 antibody to inhibit growth of prostate cancer; similar synergy is expected when other GR degraders are used in combination with anti-PD-1 antibodies, anti-PD-L1 antibodies, and other checkpoint inhibitors.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:
1. A compound of structural Formula I

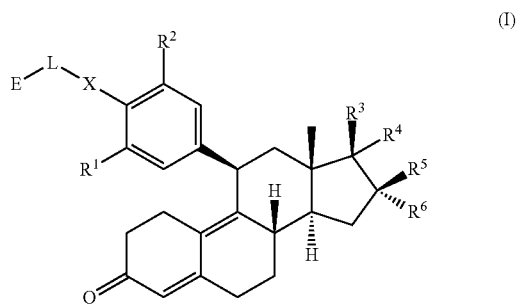

or a salt thereof, wherein:
E is chosen from

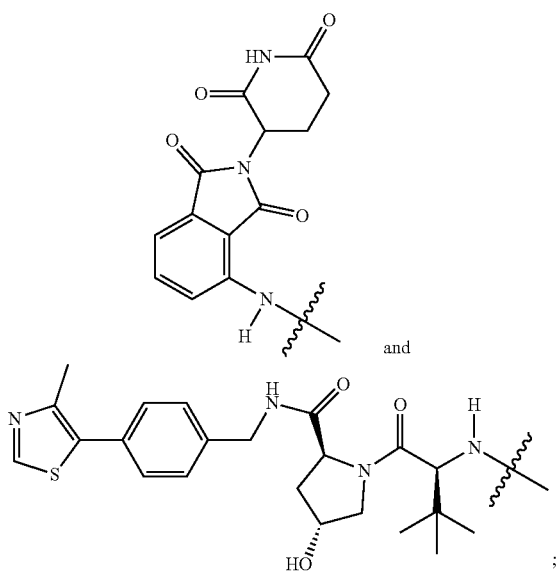

L is chosen from $*-(CH_2)_n CH_2 N(R^7)CO(CH_2)_p CH_2-**$, $*-CO(CH_2)_n CH_2-**$, $*-CO(CH_2)_q O(CH_2 CH_2 O)_n CH_2(CH_2)_p-**$, $*-(CH_2)_n CH_2-**$, $*-(CH_2)_q O(CH_2 CH_2 O)_n CH_2(CH_2)_p-**$,

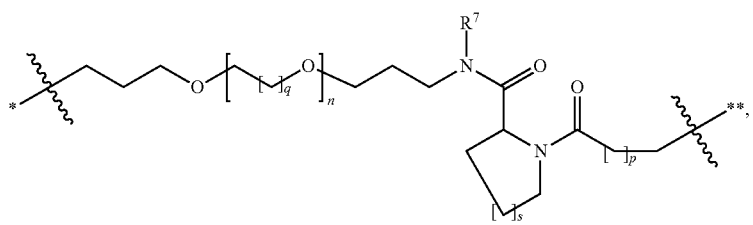

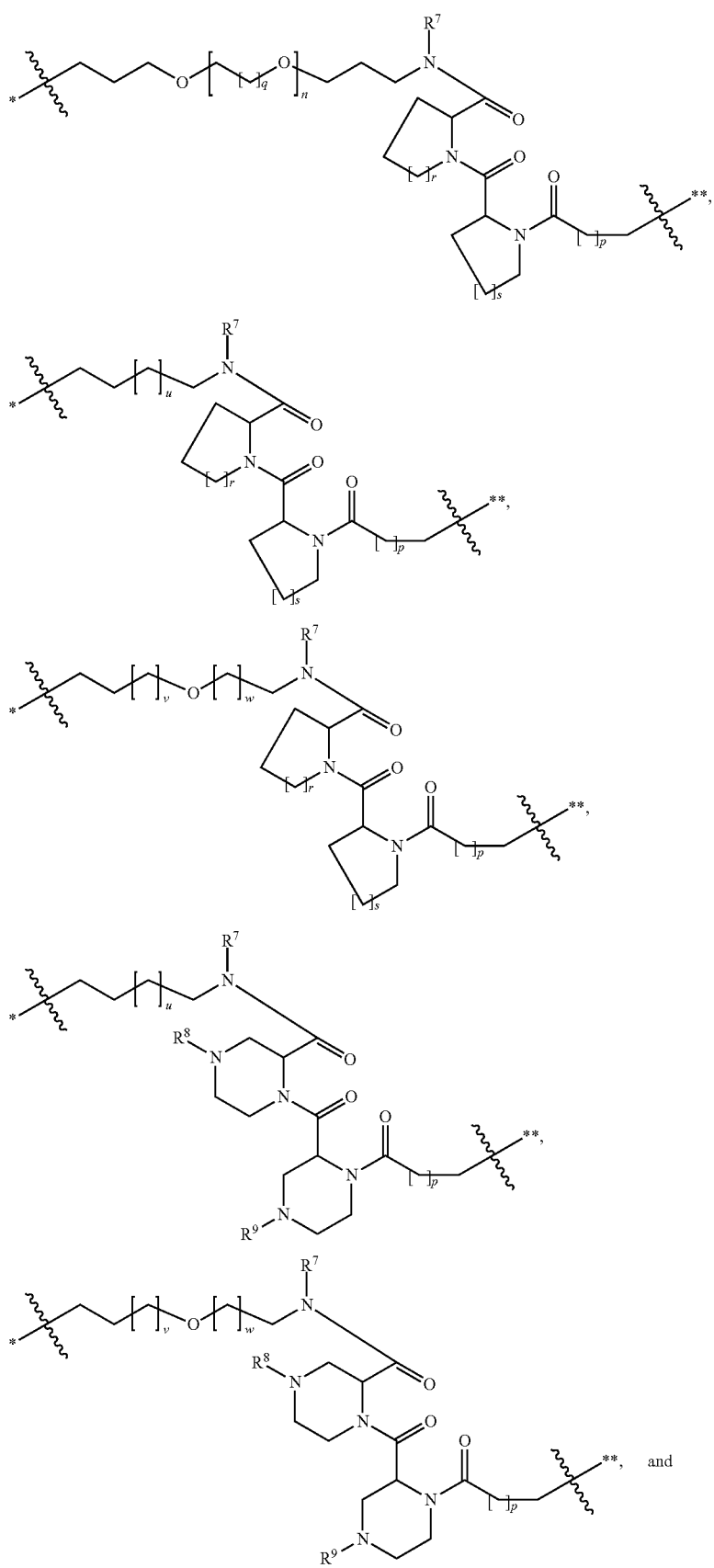

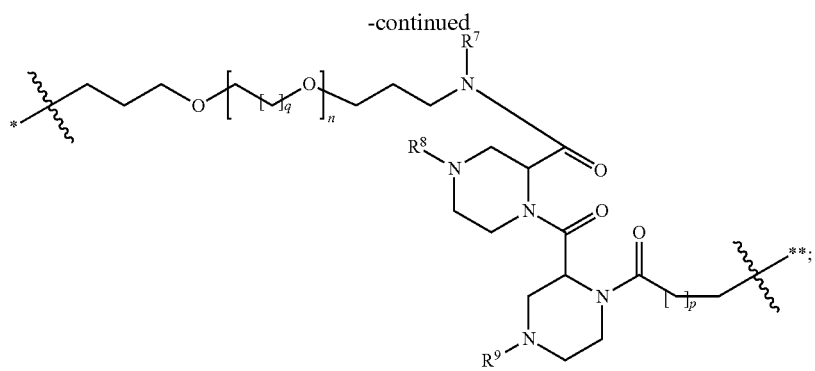

represents the point of attachment to E;
represents the point of attachment to X;
X is chosen from O, $NR^{10}$, S, SO, and $SO_2$;
$R^1$ and $R^2$ are independently chosen from H, alkyl, cycloalkyl, heterocycloalkyl, aryl, heteroaryl, alkoxy, alkenyl, alkynyl, halo, alkylamino, dialkylamino, cyano, and hydroxy;
$R^3$ and $R^4$ are independently chosen from H, alkyl, alkoxy, alkenyl, alkylnyl, and hydroxyl, or
$R^3$ and $R^4$, together with the atom to which they are attached, form a cycloalkyl or heterocycloalkyl ring, either of which is optionally substituted with 1, 2, or 3 $R^{11}$ groups;
$R^5$ and $R^6$ are independently chosen from H, alkyl, haloalkyl, alkoxy, amino, alkylamino, dialkylamino, cycloalkyl, (cycloalkyl)alkyl, heterocycloalkyl, (heterocycloalkyl)alkyl, $CONR^{12}R^{13}$, $SO_2NR^{12}R^{13}$, $SOR^{14}$, $SO_2R^{14}$, halo, hydroxy, and cyano, or
$R^5$ and $R^6$, together with the atom to which they are attached, form a cycloalkyl or heterocycloalkyl ring, either of which is optionally substituted with 1, 2, or 3 $R^{15}$ groups;
$R^7$ is chosen from H, alkyl, cycloalkyl, (cycloalkyl)alkyl, $(CH_2)_rCOOH$, alkylcarbonyl, and $-CO(CH_2)_tCOOH$;
$R^8$ and $R^9$ are independently chosen from H, alkyl, alkylcarbonyl, cycloalkylcarbonyl, alkoxycarbonyl, alkylsulfonyl, $-(CH_2)_rCOOH$, $-CO(CH_2)_tCOOH$, $-COO(CH_2)_rCOOH$, and $-(CH_2)_sSO_2OH$;
$R^{10}$ is chosen from H, alkyl, alkoxyalkyl, cycloalkyl, and heterocycloalkyl;
each $R^{11}$ is independently chosen from alkyl, cycloalkyl, heterocycloalkyl, alkoxy, cyano, halo, and hydroxy;
each $R^{12}$ and $R^{13}$ is independently chosen from H, alkyl, cycloalkyl, and heterocycloalkyl;
each $R^{14}$ is independently chosen from alkyl, cycloalkyl, and heterocycloalkyl;
each $R^{15}$ is independently chosen from alkyl, cycloalkyl, heterocycloalkyl, alkoxy, cyano, halo, and hydroxy;
n and p are independently chosen from 0-11, inclusive;
q is chosen from 0-11, inclusive;
r and s are independently chosen from 1-4, inclusive; and
t is chosen from 1-8, inclusive.

2. The compound as recited in claim 1, or a salt thereof, wherein:
$R^3$ and $R^4$ are independently chosen from H, alkyl, alkoxy, alkenyl, alkynyl, and hydroxyl, or
$R^3$ and $R^4$, together with the atom to which they are attached, form a cycloalkyl ring which is optionally substituted with 1, 2, or 3 $R^{11}$ groups, or
$R^3$ and $R^4$, together with the atom to which they are attached, form a heterocycloalkyl ring which is optionally substituted with 1, 2, or 3 $R^{11}$ groups, and which contains 1 or 2 groups selected from $-O-$, $-NH-$, $-S-$, $-SO-$, and $-SO_2-$.

3. The compound as recited in claim 2, or a salt thereof, wherein at least one of $R^3$ and $R^4$ is chosen from alkenyl and alkynyl.

4. The compound as recited in claim 3, or a salt thereof, wherein
$R^1$ and $R^2$ are independently chosen from H, alkyl, cycloalkyl, heterocycloalkyl, alkoxy, halo, alkylamino, dialkylamino, cyano, and hydroxy.

5. The compound as recited in claim 4, or a salt thereof, wherein X is $NR^{10}$.

6. The compound as recited in claim 5, or a salt thereof, wherein $R^{10}$ is chosen from H and alkyl.

7. The compound as recited in claim 6, or a salt thereof, wherein $R^7$ is chosen from H, alkyl, and cycloalkyl.

8. The compound as recited in claim 1, having structural Formula (II)

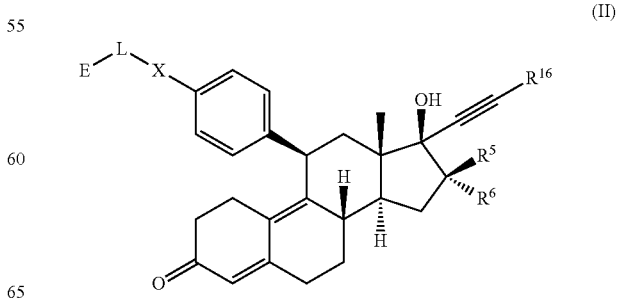

(II)

or a salt thereof, wherein:
E is chosen from
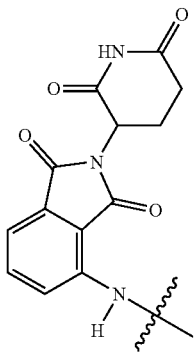
and
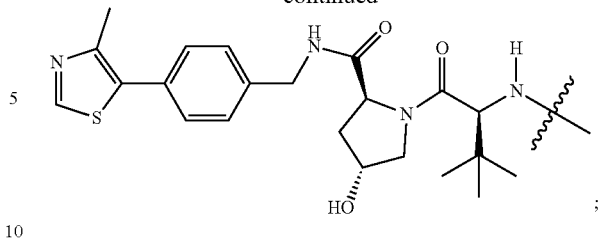
L is chosen from *—(CH$_2$)$_n$CH$_2$N(R$^7$)CO(CH$_2$)$_p$CH$_2$—**, *—CO(CH$_2$)$_n$CH$_2$—**, *—CO(CH$_2$)$_q$O(CH$_2$CH$_2$O)$_n$CH$_2$(CH$_2$)$_p$—**, *—(CH$_2$)$_n$CH$_2$—**, *—(CH$_2$)$_q$O(CH$_2$CH$_2$O)$_n$CH$_2$(CH$_2$)$_p$—**,
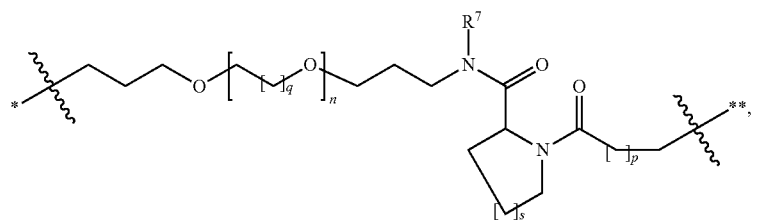
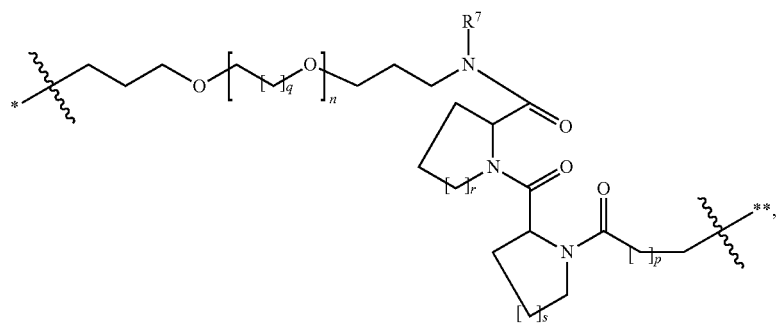
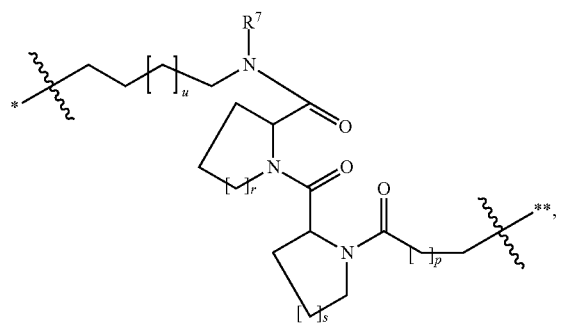
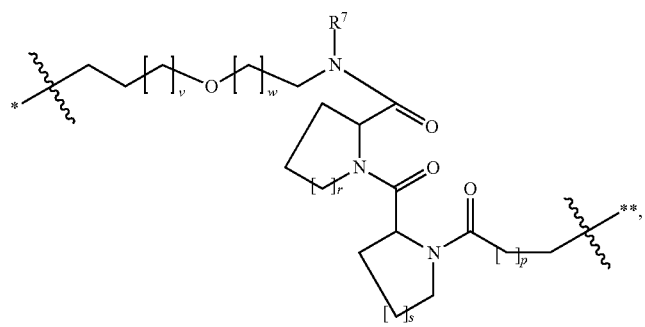

-continued

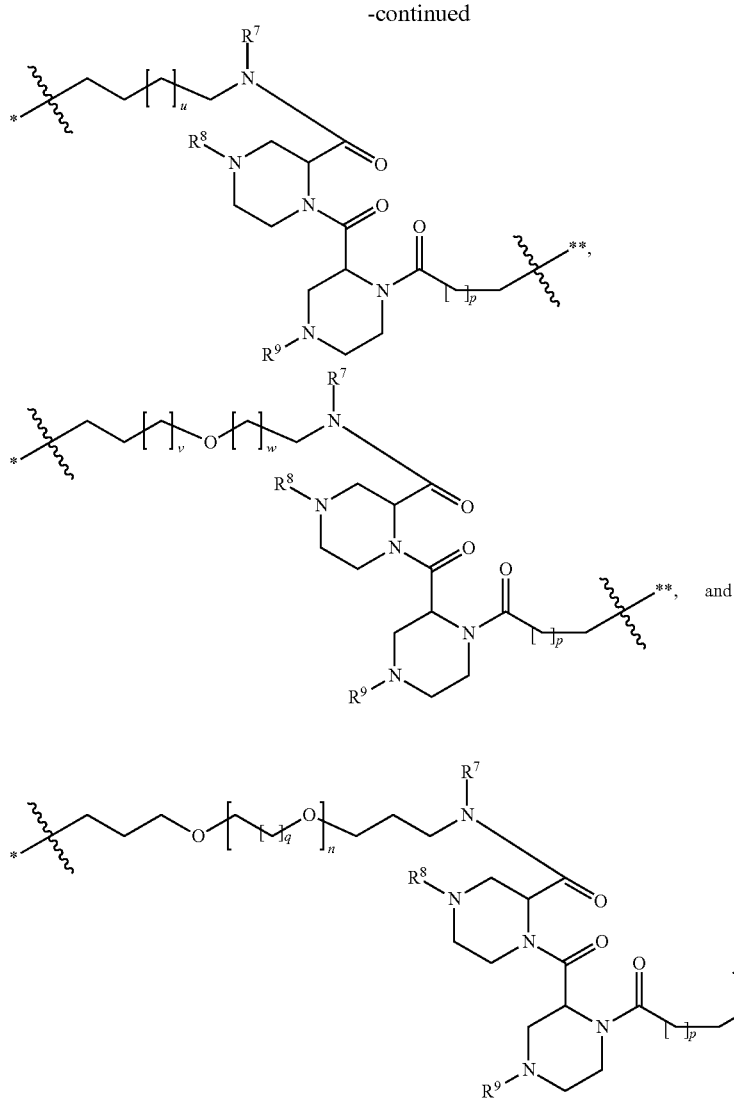

* represents the point of attachment to E;
** represents the point of attachment to X;
X is chosen from O, $NR^{10}$, S, SO, and $SO_2$;
$R^1$ and $R^2$ are independently chosen from H, alkyl, cycloalkyl, heterocycloalkyl, aryl, heteroaryl, alkoxy, alkenyl, alkynyl, halo, alkylamino, dialkylamino, cyano, and hydroxy;
$R^5$ and $R^6$ are independently chosen from H, alkyl, haloalkyl, alkoxy, amino, alkylamino, dialkylamino, cycloalkyl, (cycloalkyl)alkyl, heterocycloalkyl, (heterocycloalkyl)alkyl, $CONR^{12}R^{13}$, $SO_2NR^{12}R^{13}$, $SOR^{14}$, $SO_2R^{14}$, halo, hydroxy, and cyano, or
$R^5$ and $R^6$, together with the atom to which they are attached, form a cycloalkyl or heterocycloalkyl ring, either of which is optionally substituted with 1, 2, or 3 $R^{15}$ groups;
$R^7$ is chosen from H, alkyl, cycloalkyl, (cycloalkyl)alkyl, $(CH_2)_tCOOH$, alkylcarbonyl, and $-CO(CH_2)_tCOOH$;
$R^8$ and $R^9$ are independently chosen from H, alkyl, alkylcarbonyl, cycloalkylcarbonyl, alkoxycarbonyl, alkylsulfonyl, $-(CH_2)_tCOOH$, $-CO(CH_2)_tCOOH$, $-COO(CH_2)_tCOOH$, and $-(CH_2)_tSO_2OH$;
$R^{10}$ is chosen from H, alkyl, alkoxyalkyl, cycloalkyl, and heterocycloalkyl;
each $R^{11}$ is independently chosen from alkyl, cycloalkyl, heterocycloalkyl, alkoxy, cyano, halo, and hydroxy;
each $R^{12}$ and $R^{13}$ is independently chosen from H, alkyl, cycloalkyl, and heterocycloalkyl;
each $R^{14}$ is independently chosen from alkyl, cycloalkyl, and heterocycloalkyl;
each $R^{15}$ is independently chosen from alkyl, cycloalkyl, heterocycloalkyl, alkoxy, cyano, halo, and hydroxy;
n and p are independently chosen from 0-11, inclusive;
q is chosen from 0-11, inclusive;
r and s are independently chosen from 1-4, inclusive; and
t is chosen from 1-8, inclusive.

9. A compound chosen from
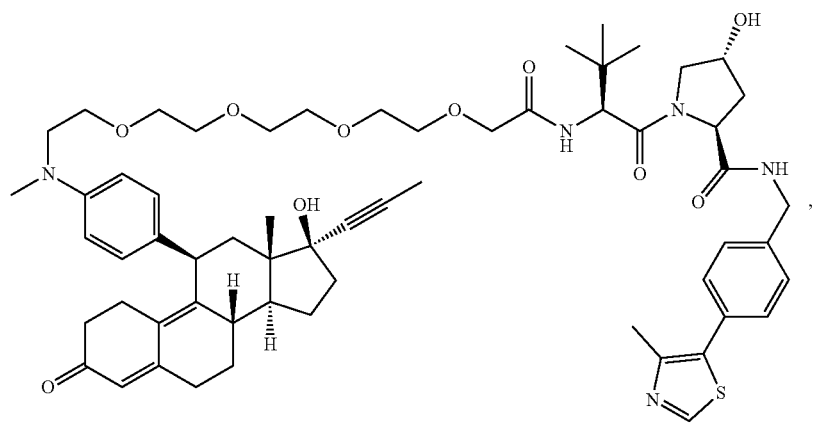
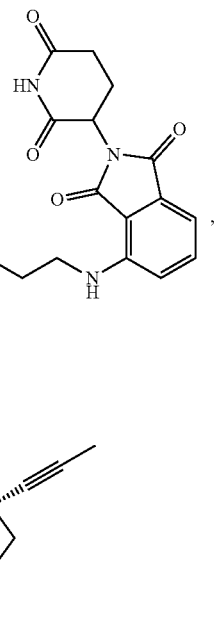

-continued

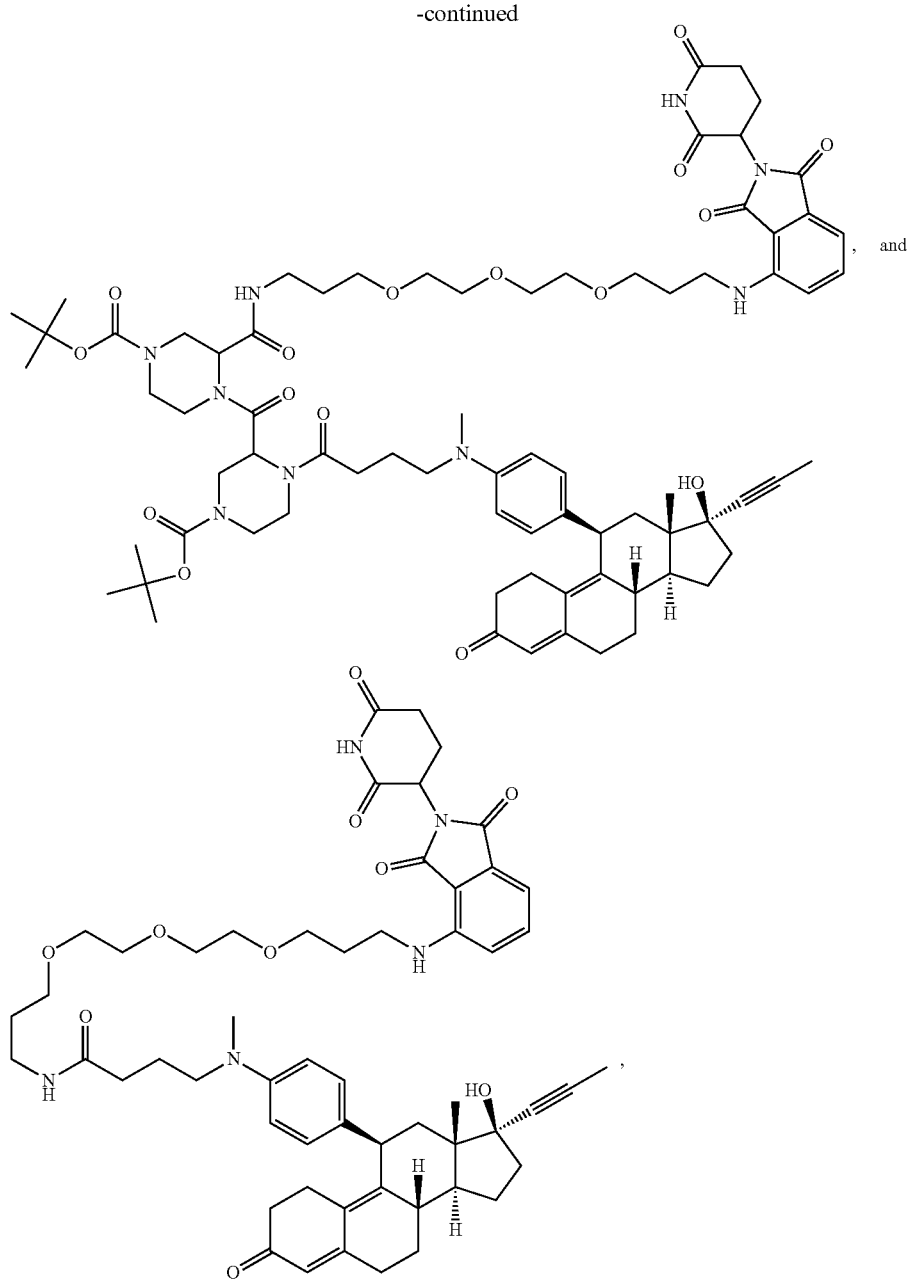

or a salt thereof.

10. A pharmaceutical composition comprising a compound as recited in claim 1, or a salt thereof, together with a pharmaceutically acceptable carrier.

11. A method of inhibition of the glucocorticoid receptor comprising contacting the glucocorticoid receptor with a compound as recited in claim 1, or a salt thereof.

12. A method of degradation of a glucocorticoid receptor comprising contacting the glucocorticoid receptor with a compound as recited in claim 1, or a salt thereof.

13. The method of degradation as recited in claim 12, wherein said degradation is selective for the glucocorticoid receptor as compared to other nuclear receptors.

14. The method of degradation as recited in claim 12, wherein said degradation does not decrease at elevated levels of said compound.

15. A method of treatment of a glucocorticoid receptor-mediated disease chosen from cancer and an inflammatory disease, comprising the administration of a therapeutically effective amount of a compound as recited in claim 1, or a salt thereof, to a patient in need thereof.

16. The method as recited in claim 15 wherein said disease is cancer.

17. The method as recited in claim 16, wherein said cancer is characterized by high expression of the glucocorticoid receptor.

18. The method as recited in claim 17, wherein said cancer is chosen from prostate cancer, breast cancer, ovarian cancer, and endometrial cancer.

19. The method as recited in claim 18, wherein said cancer is prostate cancer.

20. The method as recited in claim 19, wherein said prostate cancer is castration resistant prostate cancer.

21. The method as recited in claim 18, wherein said cancer is breast cancer.

22. The method as recited in claim 21, wherein said breast cancer is triple negative breast cancer.

23. The method as recited in claim 18, wherein said cancer is ovarian cancer.

24. The method as recited in claim 18, wherein said cancer is endometrial cancer.

25. The method as recited in claim 15, wherein said disease is an inflammatory disease.

26. The method as recited in claim 25, wherein said inflammatory disease is chosen from inflammatory bowel disease, systemic lupus erythematosus, polyarteritis nodosa, Wegener's granulomatosis, giant cell arteritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, juvenile rheumatoid arthritis, juvenile idiopathic arthritis, ankylosing spondylitis, psoriasis, plaque psoriasis, and psoriatic arthritis.

27. A method of treatment of cancer comprising the administration of:
   a. a therapeutically effective amount of a compound as recited in claim 1, or a salt thereof; and
   b. another therapeutic agent.

28. The method as recited in claim 27 wherein said other agent is chosen from Abiraterone Acetate, Apalutamide, Bicalutamide, Cabazitaxel, Casodex (Bicalutamide), Degarelix, Docetaxel, Enzalutamide, Erleada (Apalutamide), Flutamide, Goserelin Acetate, Jevtana (Cabazitaxel), Leuprolide Acetate, Lupron (Leuprolide Acetate), Lupron Depot (Leuprolide Acetate), Lupron Depot-Ped (Leuprolide Acetate), Mitoxantrone Hydrochloride, Nilandron (Nilutamide), Nilutamide, Provenge (Sipuleucel-T), Radium 223 Dichloride, Sipuleucel-T, Taxotere (Docetaxel), Viadur (Leuprolide Acetate), Xofigo (Radium 223 Dichloride), Xtandi (Enzalutamide), Zoladex (Goserelin Acetate), and Zytiga (Abiraterone Acetate).

* * * * *